United States Patent
van Bilsen et al.

(10) Patent No.: US 9,273,356 B2
(45) Date of Patent: Mar. 1, 2016

(54) METHODS AND KITS FOR LINKING POLYMORPHIC SEQUENCES TO EXPANDED REPEAT MUTATIONS

(75) Inventors: Paul van Bilsen, Maastricht (NL); William F. Kaemmerer, Edina, MN (US); Eric Burright, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 1452 days.

(21) Appl. No.: 11/752,789

(22) Filed: May 23, 2007

(65) Prior Publication Data

US 2009/0042824 A1  Feb. 12, 2009

Related U.S. Application Data

(63) Continuation-in-part of application No. 11/439,858, filed on May 24, 2006.

(51) Int. Cl.
*C12Q 1/68* (2006.01)
*C07H 21/04* (2006.01)
*C12N 15/113* (2010.01)

(52) U.S. Cl.
CPC ............ *C12Q 1/6883* (2013.01); *C12N 15/113* (2013.01); *C12Q 1/6809* (2013.01); *C12Q 1/6827* (2013.01); *C12N 2310/14* (2013.01); *C12N 2320/34* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,888,829 A | 12/1989 | Kleinerman et al. |
| 4,965,188 A | 10/1990 | Mullis et al. |
| 5,236,908 A | 8/1993 | Gruber et al. |
| 5,354,326 A | 10/1994 | Comben et al. |
| 5,496,699 A | 3/1996 | Sorenson |

(Continued)

FOREIGN PATENT DOCUMENTS

| | | |
|---|---|---|
| DE | 19938960 | 2/2001 |
| JP | 2004232811 | 8/2004 |

(Continued)

OTHER PUBLICATIONS

Miller et al. (PNAS, vol. 100, No. 12, pp. 7195-7200, Jun. 10, 2003).*

(Continued)

*Primary Examiner* — Jeanine A Goldberg
(74) *Attorney, Agent, or Firm* — Fox Rothschild LLP; Gerard P. Norton; Jianming J. Hao

(57) ABSTRACT

Methods and kits are provided for determining which single nucleotide polymorphism ("SNP") variant of an allele of a heterozygous patient is on the same allele as a disease-causing mutation that is at a remote region of the gene's mRNA comprising a) an allele specific reverse transcription reaction using an allele specific primer which recognizes one SNP variant, wherein further the 3' end of the primer is positioned at the SNP nucleotide position, and b) analysis of the resulting cDNA product from the reverse transcription reaction at the region of the mutation to determine the presence or absence of the mutation on this allele specific cDNA product, wherein the allele specific primer is shorter than about 20 nucleotides.

15 Claims, 5 Drawing Sheets

(56) References Cited

U.S. PATENT DOCUMENTS

| | | |
|---|---|---|
| 5,534,350 A | 7/1996 | Liou |
| 5,624,803 A | 4/1997 | Noonberg et al. |
| 5,639,275 A | 6/1997 | Baetge et al. |
| 5,702,716 A | 12/1997 | Dunn et al. |
| 5,720,720 A | 2/1998 | Laske et al. |
| 5,735,814 A | 4/1998 | Elsberry et al. |
| 5,782,892 A | 7/1998 | Castle et al. |
| 5,800,390 A | 9/1998 | Hayakawa et al. |
| 5,814,014 A | 9/1998 | Elsberry et al. |
| 5,840,059 A | 11/1998 | March et al. |
| 5,882,561 A | 3/1999 | Barsoum et al. |
| 5,925,310 A | 7/1999 | Nakayama et al. |
| 5,942,455 A | 8/1999 | Barsoum et al. |
| 5,968,059 A | 10/1999 | Ellis et al. |
| 5,985,561 A * | 11/1999 | Kimberly et al. ................. 435/6 |
| 5,997,525 A | 12/1999 | March et al. |
| 6,013,431 A | 1/2000 | Soderlund et al. |
| 6,042,579 A | 3/2000 | Elsberry et al. |
| 6,093,180 A | 7/2000 | Elsberry |
| 6,110,459 A | 8/2000 | Mickle et al. |
| 6,151,525 A | 11/2000 | Soykan et al. |
| 6,156,503 A | 12/2000 | Drazen et al. |
| 6,180,613 B1 | 1/2001 | Kaplitt et al. |
| 6,187,906 B1 | 2/2001 | Gluckman et al. |
| 6,207,425 B1 | 3/2001 | Liu et al. |
| 6,231,969 B1 | 5/2001 | Knight et al. |
| 6,245,884 B1 | 6/2001 | Hook |
| 6,251,589 B1 * | 6/2001 | Tsuji et al. ................. 435/6 |
| 6,281,009 B1 | 8/2001 | Boyce |
| 6,291,243 B1 | 9/2001 | Fogarty et al. |
| 6,294,202 B1 | 9/2001 | Burns et al. |
| 6,300,539 B1 | 10/2001 | Morris |
| 6,309,634 B1 | 10/2001 | Bankiewicz et al. |
| 6,310,048 B1 | 10/2001 | Kumar |
| 6,313,268 B1 | 11/2001 | Hook |
| 6,319,905 B1 | 11/2001 | Mandel et al. |
| 6,343,233 B1 | 1/2002 | Werner et al. |
| 6,372,250 B1 | 4/2002 | Pardridge |
| 6,372,721 B1 | 4/2002 | Neuman et al. |
| 6,376,471 B1 | 4/2002 | Lawrence, III et al. |
| 6,436,392 B1 | 8/2002 | Engelhardt et al. |
| 6,436,708 B1 | 8/2002 | Leone et al. |
| 6,461,989 B1 | 10/2002 | El-Raghy et al. |
| 6,468,524 B1 | 10/2002 | Chiorini et al. |
| 6,551,290 B1 | 4/2003 | Elsberry et al. |
| 6,594,880 B2 | 7/2003 | Elsberry |
| 6,609,020 B2 | 8/2003 | Gill |
| 6,632,671 B2 | 10/2003 | Unger |
| 6,659,995 B1 | 12/2003 | Taheri |
| 6,870,030 B2 | 3/2005 | Powell et al. |
| 6,945,969 B1 | 9/2005 | Morris et al. |
| 7,320,965 B2 | 1/2008 | Sah et al. |
| 7,645,576 B2 * | 1/2010 | Lo et al. ................. 435/6.11 |
| 2001/0027309 A1 | 10/2001 | Elsberry |
| 2001/0031947 A1 | 10/2001 | Heruth |
| 2002/0004038 A1 | 1/2002 | Baugh et al. |
| 2002/0068093 A1 | 6/2002 | Trogolo et al. |
| 2002/0114780 A1 | 8/2002 | Bankiewicz |
| 2002/0141980 A1 | 10/2002 | Bankiewicz |
| 2002/0187127 A1 | 12/2002 | Bankiewicz |
| 2003/0039964 A1 | 2/2003 | Giffard et al. |
| 2003/0078229 A1 | 4/2003 | Cooper et al. |
| 2003/0088236 A1 | 5/2003 | Johnson et al. |
| 2003/0092003 A1 | 5/2003 | Blatt et al. |
| 2003/0095958 A1 | 5/2003 | Bhisetti et al. |
| 2003/0109476 A1 | 6/2003 | Kmiec et al. |
| 2003/0120282 A1 | 6/2003 | Scouten et al. |
| 2003/0143732 A1 | 7/2003 | Fosnaugh et al. |
| 2003/0152947 A1 | 8/2003 | Crossman et al. |
| 2003/0175772 A1 | 9/2003 | Wang |
| 2003/0190635 A1 | 10/2003 | McSwiggen |
| 2003/0224512 A1 | 12/2003 | Dobie |
| 2003/0232353 A1* | 12/2003 | Kennedy ................. 435/6 |
| 2004/0018520 A1 | 1/2004 | Thompson |
| 2004/0023390 A1 | 2/2004 | Davidson |
| 2004/0023855 A1 | 2/2004 | John et al. |
| 2004/0048301 A1 | 3/2004 | Sood et al. |
| 2004/0186422 A1 | 9/2004 | Rioux |
| 2004/0215164 A1 | 10/2004 | Abbott |
| 2004/0220132 A1 | 11/2004 | Kaemmerer |
| 2004/0241854 A1 | 12/2004 | Davidson et al. |
| 2004/0258666 A1 | 12/2004 | Passini |
| 2004/0259247 A1 | 12/2004 | Tuschl |
| 2004/0265849 A1 | 12/2004 | Cargill |
| 2004/0266707 A1 | 12/2004 | Leake |
| 2005/0032733 A1 | 2/2005 | McSwiggen |
| 2005/0042646 A1 | 2/2005 | Davidson |
| 2005/0048641 A1 | 3/2005 | Hildebrand |
| 2005/0096284 A1 | 5/2005 | McSwiggen |
| 2005/0137134 A1 | 6/2005 | Gill |
| 2005/0153353 A1 | 7/2005 | Meibohm |
| 2005/0158754 A1 | 7/2005 | Puffenberger et al. |
| 2005/0177866 A1* | 8/2005 | Kirsch ................. 726/3 |
| 2005/0180955 A1 | 8/2005 | Bankiewicz |
| 2005/0202075 A1 | 9/2005 | Pardridge |
| 2005/0209179 A1 | 9/2005 | McSwiggen |
| 2005/0255086 A1 | 11/2005 | Davidson |
| 2005/0282198 A1 | 12/2005 | Duff |
| 2006/0009408 A1 | 1/2006 | Davidson et al. |
| 2006/0014165 A1 | 1/2006 | Hakonarson |
| 2006/0041242 A1 | 2/2006 | Stypulkowski |
| 2006/0150747 A1 | 7/2006 | Mallett |
| 2006/0210538 A1 | 9/2006 | Kaplitt et al. |
| 2006/0224411 A1 | 10/2006 | Chang |
| 2006/0257912 A1 | 11/2006 | Kaemmerer |
| 2007/0031844 A1 | 2/2007 | Khvorova et al. |
| 2007/0161590 A1 | 7/2007 | Van Bilsen et al. |
| 2007/0184029 A1 | 8/2007 | Mishra |
| 2007/0184457 A1* | 8/2007 | Pont-Kingdon et al. ........ 435/6 |
| 2008/0113351 A1 | 5/2008 | Naito |
| 2009/0022864 A1 | 1/2009 | Steenhof |

FOREIGN PATENT DOCUMENTS

| | | |
|---|---|---|
| WO | WO9220400 | 11/1992 |
| WO | WO9323569 | 11/1993 |
| WO | WO9402595 | 2/1994 |
| WO | WO9618736 | 6/1996 |
| WO | WO9740847 | 11/1997 |
| WO | WO98/20166 A2 | 5/1998 |
| WO | WO9846273 | 10/1998 |
| WO | WO9846740 | 10/1998 |
| WO | WO9939744 | 8/1999 |
| WO | WO9950300 | 10/1999 |
| WO | WO0030567 | 6/2000 |
| WO | WO00/64505 | 11/2000 |
| WO | WO0116312 | 3/2001 |
| WO | WO0149844 | 7/2001 |
| WO | WO0160794 | 8/2001 |
| WO | WO0170276 | 9/2001 |
| WO | WO0180840 | 11/2001 |
| WO | WO0191801 | 12/2001 |
| WO | WO0205804 | 1/2002 |
| WO | WO0207810 | 1/2002 |
| WO | WO0222177 | 3/2002 |
| WO | WO03042385 | 5/2003 |
| WO | WO03047676 | 6/2003 |
| WO | WO03053516 | 7/2003 |
| WO | WO03070895 | 8/2003 |
| WO | WO03/100101 A1 | 12/2003 |
| WO | WO03099298 | 12/2003 |
| WO | WO03102131 | 12/2003 |
| WO | WO2004007718 | 1/2004 |
| WO | WO2004010787 | 2/2004 |
| WO | WO2004013280 | 2/2004 |
| WO | WO2004013355 | 2/2004 |
| WO | WO2004041101 | 5/2004 |
| WO | WO2004047872 | 6/2004 |
| WO | WO2004058940 | 7/2004 |
| WO | WO2004084955 | 10/2004 |
| WO | WO2004098648 | 11/2004 |
| WO | WO2004101063 | 11/2004 |
| WO | 2005/027980 A1 | 3/2005 |
| WO | WO2005027980 | 3/2005 |

(56) References Cited

FOREIGN PATENT DOCUMENTS

| WO | WO2005045034 | 5/2005 |
|---|---|---|
| WO | WO2005116204 | 8/2005 |
| WO | 2005105995 | 11/2005 |
| WO | WO2005120581 | 12/2005 |
| WO | WO2006022639 | 3/2006 |
| WO | 2007/002904 A2 | 4/2007 |
| WO | WO2007039721 | 4/2007 |
| WO | WO2008005562 | 7/2007 |
| WO | WO2007087451 | 8/2007 |
| WO | WO2007139811 | 12/2007 |
| WO | WO2008004260 | 1/2008 |
| WO | WO2008021157 | 2/2008 |
| WO | WO2008046273 | 4/2008 |
| WO | WO2008143774 | 11/2008 |

OTHER PUBLICATIONS

Okuda et al. (J. Human Genetics, vol. 47, pp. 387-394, 2002).*
Lee et al. 1999. Tsix, a gene antisense to Xist at the X-inactivation centre. Nat Genet 21(4):400-404.*
Chen et al., "Sleeping Beauty-mediated down-regulation of huntingtin expression by RNA interference," BBRC 329 (2005), pp. 646-652.
Miller et al., "Targeting alzheimer's disease genes with RNA interference: an efficient strategy for silencing mutant alleles," Nucleic Acids Research (2004): vol. 32, No. 2, pp. 661-668.
Miller et al., "Allele-specific silencing of dominant disease genes," PNAS (2003): vol. 100, No. 12, pp. 7195-7200.
Aebisher, Trends in Neurosci. 24(9) 553-540 (Sep. 2001).
Altschul et al., "Gapped BLAST and PSO-BLAST: a new generation of protein database search prorams," Nucl. Acids Res., 25(17): 3389-3402 (1997).
Ambion Inc., pSilencer™ 1.0-U6 siRNA Expression Vector, Catalog # 7207-20 µg, Nov. 2004, Austin, TX, 6 pgs.
Ambion Technical Bulletin #506 (as published on Nov. 16, 2002) downloaded from www.archive.org.
Ambion, Inc., Silencer siRNA® Construction Kit, Cat. #1620, Instruction Manual, Aug. 2005, 36 pgs.
Ausubel et al., Eds., Current Protocols in Molecular Biology, vol. 1-3, John Wiley & Sons, Inc., New York, NY, 1994; title page, publisher's page and table of contents only, 14 pgs.
Basi et al., "Antagonistic Effects of β-site Amyloid Precursor Protein-cleaving Enzymes 1 and 2 on β-Amyloid Peptide Production in Cells," J. Bio. Chem., Published, JBC Papers in Press, Jun. 2003; 278(34): 31512-31520.
Bass et al., Nature 411: 428-429 (2001).
Bertrand et al., Biochem Biophys Res Comm 296: 1000-1004 (2002).
Bodendorf et al., J. Neurochem. 80(5), 799-806 (Mar. 2002).
Boillée et al., "Gene therapy for ALS deliver," Trends in Neurosciences, May 2004; 27(5): 235-238.
Bortolin, Susan et al., "Analytical validation of the tag-it high-throughout microsphere-based universal array genotyping platform. Application to the multiplex detection of a panel of thrombophilia-associates single-nucleotide polymorphisms." American Association for Clinical Chemistry vol. 50(11) 2028-2036 (2004).
Brentano et al., P.N.A.S. 89:4099-4103 (1992).
Brummelkamp et al Science 296: 550-553 (2002).
Burger et al., Mol. Ther. 10(2) 302-317 (Aug. 2004).
Cahill et al Atlas of Human Cross-Sectional Anatomy Wiley-Liss, 3rd Ed. (1995).
Cai et al Nat. Neurosci. 4(3) 233-234 (2004).
Callahan Am. J. Pathol. 158(3) 1173-1177 (2001).
Caplen et al, Human Mol. Genet. 11(2) 175-184 (2002).
Chen et al., Nucl. Acid. Res. 20, 4581-4589 (1992).
Chi et al., "Genomewide view of gene silencing by small interfering RNAs," Proc. Natl. Acad. Sci. USA, May 2003; 100 (11): 6343-6346.
Chowhira et al., J. Biol. Chem. 269, 25856-25863 (1994).
Christman, Tissue Engineering (10) 403-409 (2004).
Cioffi et al., Biochem J. 365: 833-840 (2002).
Clark et al., Annals Int. Med. 138 400-411 (2003).

Clark et al., J. Neurosci. 17(19) 7385-7395 (1997).
Cleary et al., Nat. Neurosci. 8(1) 79-84 (ePub Dec. 19, 2004).
Couture et al., Trends in Genetics, 12(12) 510-515 (Dec. 1996).
Dai et al., Developmental Biology 285:80-90 (2005).
Davidson et al., The Lancet, Neurology 3, 145-149 (2004).
Demetriades J. Neurolog. Sci. 203-204, 247-251 (2002).
Dineley, J, Biol. Chem. 277 (25) 22768-22780 (2002).
Dorri et al., Exp. Neurology 147 48-54 (1997).
Dropulic et al., J. Virol. 66(1) 1432-1441 (1992).
During et al., "Subthalamic GAD GeneTransfer in Parkinson's Disease Patients Who Are Candidates for Deep Brain Stimulation," Human Gene Therapy, Aug. 2001; 12(12): 1587-1598.
ElBashir, EMBOJ 20(23) 6877-6888 (2001).
Ezrin-Waters et al., Can. J. Neurol. Sci. 13, 8-14 (1986).
Fu et al., Mo. Ther. 8(6) 911-917 (Dec. 2003).
Gau, Am. J. Pathol., 160(2) 731-738 (2002).
GeneDetect.com Limited, Code GD100X-RV, (GeneDetect rAVE™ gene delivery reagent), copyright 2000-2002, Auckland, New Zealand, 2 pgs.
Geraerts et al., Concise Review: Therapeutic Strategies for Parkinson Disease Based on Modulation of Adult Neurogenesis. Stem Cells, Nov. 2, 2006, vol. 25, No. 2, pp. 263-270.
Gerlai Behay. Brain Res. 95 191-203 (1998).
Glorioso, Curr. Opinion in Drug Discovery & Dev't 5(2) Pharma Press ISSN 1367-6733 (2002).
Good et al., Gene Ther. 4: 45-54 (1997).
Goto et al., Neurology, 60(5) Suppl. 1 p. A286 (Mar. 11, 2003).
Harrison et al., Mol. Cel. Neurosci. 24(3) 646-655 (2003).
Hartlage-Rubsamen et al., Glia 41(2) 169-179 (Dec. 28, 2002).
Heale et al., Nucl. Acid. Res. 22(3), 2005.
Holen et al., Nucl. Acid Res. 30:1757-1766 (2002).
Hommel et al., "Local gene knockdown in the brain using viral-mediated RNA interference," Nature Medicine, Dec. 2003; 9(12); 1539-1544.
Hommel et al., Society for Neuroscience Abstract, 2003, Abstract 325.14 (2003).
Hooper et al., Neuroscience 63, 917-924 (1995).
Hsiao et al, Science 274 99-102(1996).
Huwyler et al., "Brain drug delivery of small molecules using immunoliposomes,"Proc. Natl. Acad., USA, Nov. 1996;93:14164-14169.
Invitrogen, pShooter™ Vector (pCMV/myc © vectors), for the intracellular targeting of recombinant proteins and antibodies, Catalog Nos. V820-20, V821-20, V822-20, V823-20, Version E, copyright 1998-2001, 35 pgs.
Invitrogen, pTRACER™-CMV2, Catalog Nos. V885-01, V885-20, Version C, copyright 1998-2001, 21 pgs.
Isacson et al., Scandinavian Physiol. Society 179 173-177 (2003).
Izant et al., Science 299 345 (1985).
Kaemmerer et al., Soc. Neurosci. Meeting (Oct. 26, 2004).
Kao et al., "BACE1 Suppression by RNA Interference in Primary Cortical Neurons," J. Bio. Chem., Published, JBC Papers in Press, Nov. 2003, 2004; 279(3): 1942-1949.
Kashani-Sabet et al., Antisense Res. Dev. 2: 3-15 (1992).
Katz et al., Bioessays 11(6): 181-185 (Dec. 1989).
Kawarabayashi et al., J. Neurosci. 372-381 (2001).
Kenderell et al., (2000) Nat. Biotech. 17, 896-898 (2000).
King et al., Physiology & Behavior, 75: 627-642, 2002.
Kitabwala et al., New England J. Med. 347(17) 1364-1367 (Oct. 24, 2002).
Kitazume J. Biol. Chem. 280(9) 8589-8595 (Mar. 4, 2005).
Klement et al., Cell 95 41-53 (1998).
L'Huillier et al., EMBO J. 11(12), 4411-4418 (1992).
Laird et al., J. Neurosci. 25, 11693-11709 (Dec. 14, 2005).
Le Gal La Salle et al, Science 259, 988-990 (1993).
Li et al., Mol. Cell Bio. 22 (5) 1277-1287 (2002).
Lisziewicz et al., Proc. Nat. Acad. Sci 90 8000-8004 (Sep. 1993).
Liu et al., Proc. Japan Academy, Series B, Physical and Biol. Sciences 79(10) 293-298 (Dec. 1993).
Luo et al., Neurobiol. Dis. 14(1), 81-88 (Oct. 2003).
Li et al., "Predicting siRNA efficiency," Cell. Mol. Life Sci. 64 (2007), pp. 1785-1792.
Luo, Nat. Neurosci. 4, 231-232 (2001).

(56) References Cited

OTHER PUBLICATIONS

MacDonald, M. et al., "A novel gene containing a trinucleotide repeat that is expanded and unstable on huntington's disease chromosomes," Cell, vol. 72, 971-983 (1993).
Mas-Monteys, A. et al., "Allele-Specific silencing of mutant huntingtin for huntington's disease therapy", Molecular Therapy 13: S274-S275 (2006).
Matilla et al., J. Neurosci 18, 5508-5516 (1998).
McGarry et al., Proc. Natl Acad. Sci. 83, 399-403 (1986).
McManus et al., Nature Reviews/Genetics 3, 737-747 (Oct. 2002).
Menei et al Neurosurgery 34: 1058-1064 (1994).
Messier et al., Pharm. Biochem Behavior 63 313-318 (1999).
Miller et al Proc. Nat. Acad. Sci. 100(12) 7195-7200 (Jun. 10, 2003).
Mirus, TransIT-Neural® Transfection Reagent, Product Nos. MIR 2144, MIR 2140, MIR 2145, MIR 2146, Lit. # ML022, Rev. Mar. 2, 2005, 5 pgs.
Mirus, TransIT-TKO® Transfection Reagent, Product Nos. MIR 2154, MIR 2150, MIR 2155, MIR 2156, Lit. # ML015, Rev. Jul. 2004, 6 pgs.
Mogan et al., JECT 36: 191-196 (2004).
Morel et al., J. Comparative Neurology 387, 588-630 (1997).
Mucke et al., J. Neurosci. 20(11) 4050-4058 (Jun. 1, 2000).
Naldini et al. Proc. Nat. Acad. Sci. 93, 11382-11388 (Oct. 1996).
National Center for Biotechnology Information, National Library of Medicine, National Institutes of Health, "What does NCBI do?" [online]. Bethesda, MD [retrieved on Dec. 5, 2005], Revised Dec. 2005. Retrieved from the Internet: <URL:http://www.ncbi.nlm.nih.gov>, 2 pgs.
National Center for Biotechnology Information, National Library of Medicine, National Institutes of Health, GenBank Locus AF163864, Accession No. AF163864, "*Homo sapiens* SNCA isoform (SNCA) gene, complete cds, alternatively spliced," [online]. Bethesda, MD [retrieved on Jun. 21, 2004]. Retrieved from the Internet: <URL:http://www.ncbi.nlm.nih.gov/entrez/viewer.fcgi?db=nucleotide&val=11118351>; 43 pgs.
National Center for Biotechnology Information, National Library of Medicine, National Institutes of Health, GenBank Locus AF163865, Accession No. AF163865, "Mus musculus alpha-synuclein (Snca) gene, complete cds," [online]. Bethesda, MD [retrieved on Jun. 21, 2004]. Retrieved from the Internet:<URL:http://www.ncbi.nlm.nih.gov/entrez/viewer.fcgi?db=nucleotide&val=11118354>; 33 pgs.
National Center for Biotechnology Information, National Library of Medicine, National Institutes of Health, GenBank Locus AH003045, Accession No. AH003045, "*Homo sapiens* huntingtin (HD) gene, exon 1," [online]. Bethesda, MD [retrieved on May 3, 2005]. Retrieved from the Internet:<URL:http://www.ncbi.nlm.nih.gov/entrez/viewer.fcgi?db=nucleotide&val=663286>; 42 pgs.
National Center for Biotechnology Information, National Library of Medicine, National Institutes of Health, GenBank Locus NM_000027, Accession No. NM_000027, "*Homo sapiens* aspartylglucosaminidase (AGA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=32313568>; 4 pgs.
National Center for Biotechnology Information, National Library of Medicine, National Institutes of Health, GenBank Locus NM_000046, Accession No. NM_000046, "*Homo sapiens* arylsulfatase B (ARSB), transcript variant 1, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=38569404>; 4 pgs.
National Center for Biotechnology Information, National Library of Medicine, National Institutes of Health, GenBank Locus NM_000049, Accession No. NM_000049, "*Homo sapiens* aspartoacylase (aminoacylase 1, Canavan disease) (ASPAS), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557334>; 4 pgs.
National Center for Biotechnology Information, National Library of Medicine, National Institutes of Health, GenBank Locus NM_000147, Accession No. NM_000147, "*Homo sapiens* fucosidase, alpha-L1, tissue (FUCA1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=24475878>; 3 pgs.
National Center for Biotechnology Information, National Library of Medicine, National Institutes of Health, GenBank Locus NM_000152, Accession No. NM_000152, "*Homo sapiens* glucosidase, alpha; acid (Pompe disease, glycogen storage disease type II) (GAA), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=11496988>; 4 pgs.
National Center for Biotechnology Information, National Library of Medicine, National Institutes of Health, GenBank Locus NM_000153, Accession No. NM_000153, "*Homo sapiens* galactosylceramidase (Krabbe disease) (GALC), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557612>; 5 pgs.
National Center for Biotechnology Information, National Library of Medicine, National Institutes of Health, GenBank Locus NM_000157, Accession No. NM_000157, "*Homo sapiens* glucosidase, beta; acid (includes glucosylceramidase) (GBA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4503934>: 7 pgs.
National Center for Biotechnology Information, National Library of Medicine, National Institutes of Health, GenBank Locus NM_000158, Accession No. NM_000158, "*Homo sapiens* glucan (1, 4-alpha-), branching enzyme 1 (glycogen branching enzyme, Andersen disease, glycogen storage disease trype (IV)(GBE1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557618>; 2 pgs.
National Center for Biotechnology Information, National Library of Medicine, National Institutes of Health, GenBank Locus NM_000181, Accession No. NM_000181, "*Homo sapiens* glucuronidase, beta (GUSB), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4504222>; 4 pgs.
National Center for Biotechnology Information, National Library of Medicine, National Institutes of Health, GenBank Locus NM_000199, Accession No. NM_000199, "*Homo sapiens* N-sulfoglucosamine sulfohydrolase (sulfamidase) (SGSH), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=31543619>; 3 pgs.
National Center for Biotechnology Information, National Library of Medicine, National Institutes of Health, GenBank Locus NM_000202, Accession No. NM_000202, "*Homo sapiens* iduronate 2-sulfatase (Hunter syndrome)(ID), transcript variant 1, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=5360215>; 8 pgs.
National Center for Biotechnology Information, National Library of Medicine, National Institutes of Health, GenBank Locus NM_000203, Accession No. NM_000203, "*Homo sapiens* iduronidase, alpha-L-(IDUA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40354208>; 6 pgs.
National Center for Biotechnology Information, National Library of Medicine, National Institutes of Health, GenBank Locus NM_000235, Accession No. NM_000235, "*Homo sapiens* lipase A, lysosomal acid, cholesterol esterase (Wolman disease) (LIPA), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=4557720>; 4 pgs.
National Center for Biotechnology Information, National Library of Medicine, National Institutes of Health, GenBank Locus NM_000262, Accession No. NM_000262, "*Homo sapiens* N-acetylgalactosaminidase, alpha-(NAGA), mRNA," [online].

(56) References Cited

OTHER PUBLICATIONS

Bethesda, MD [retrieved on Mar. 5, 2009]. Retrieved from the Internet:<URL:http://www.ncbi.nlm.nih.gov/entrez/viewer.fcgi?db=nucleotide&val=4557780>; 4 pgs.

National Center for Biotechnology Information, National Library of Medicine, National Institutes of Health, GenBank Locus NM_000263, Accession No. NM_000263, "*Homo sapiens* N-acetylglucosaminidase, alpha-(Sanfilippo disease) (IIIB)(NAGLU), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40548380>; 4 pgs.

National Center for Biotechnology Information, National Library of Medicine, National Institutes of Health, GenBank Locus NM_000310, Accession No. NM_000310, "*Homo sapiens* palmitoyl-protein thioesterase 1 (ceroid-lipofuscinosis, neuronal 1, infantile) (PPT1), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=4506030>; 4 pgs.

National Center for Biotechnology Information, National Library of Medicine, National Institutes of Health, GenBank Locus NM_000332, Accession No. NM_000332, "*Homo sapiens* spinocerebellar ataxia 1 (olivopontocerebellar ataxia 1, autosomal dominant, ataxin 1) (SCA1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4506792>; 7 pgs.

National Center for Biotechnology Information, National Library of Medicine, National Institutes of Health, GenBank Locus NM_000345, Accession No. NM_000345, "*Homo sapiens* synuclein, alpha (nonA4 component of amyloid precursor) (SNCA), transcript variant NACP140, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=6806896>; 6 pgs.

National Center for Biotechnology Information, National Library of Medicine, National Institutes of Health, GenBank Locus NM_000404, Accession No. NM_000404, "*Homo sapiens* glactosidase, beta 1 (GLB1), transcript variant 179423, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=10834965>; 5 pgs.

National Center for Biotechnology Information, National Library of Medicine, National Institutes of Health, GenBank Locus NM_000434, Accession No. NM_000434, "*Homo sapiens* sialidase 1 (lysosomal sialidase)(NEU1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40806202>: 5 pgs.

National Center for Biotechnology Information, National Library of Medicine, National Institutes of Health, GenBank Locus NM_000487, Accession No. NM_000487, "*Homo sapiens* arysulfatase A (ARSA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=7262293>; 4 pgs.

National Center for Biotechnology Information, National Library of Medicine, National Institutes of Health, GenBank Locus NM_000512, Accession No. NM_000512, "*Homo sapiens* galactosamine (N-acetyl)-6-sulfate sulfatase (Morquio syndrome, mucopolysaccharidosis type IVA), (GALNS), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=9945384>; 4 pgs.

National Center for Biotechnology Information, National Library of Medicine, National Institutes of Health, GenBank Locus NM_000520, Accession No. NM_000520, "*Homo sapiens* hexosaminidase A (alpha polypeptide) (HEXA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13128865>; 5 pgs.

National Center for Biotechnology Information, National Library of Medicine, National Institutes of Health, GenBank Locus NM_000521, Accession No. NM_000521, "*Homo sapiens* hexosaminidase B (beta polypeptide) (HEXB), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13128866>; 6 pgs.

National Center for Biotechnology Information, National Library of Medicine, National Institutes of Health, GenBank Locus NM_000528, Accession No. NM_000528, "*Homo sapiens* mannosidase, alpha, class 2B, member 1 (MAN2B1), mRNA," [online]. Bethesda, MD [retrieved on Mar. 5, 2009]. Retrieved from the Internet:<URL:http://mm.ncbi.nlm.nih.gov/entrez/viewer.fcgi?db=nucleotide&val=10834967>; 4 pgs.

National Center for Biotechnology Information, National Library of Medicine, National Institutes of Health, GenBank Locus NM_000543, Accession No. NM_000543, "*Homo sapiens* sphingomyelin phosphodiesterase 1 acid lysosomal (acid sphingomyelinase) (SMPD1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40254417>: 5 pgs.

National Center for Biotechnology Information, National Library of Medicine, National Institutes of Health, GenBank Locus NM_002076, Accession No. NM_002076, "*Homo sapiens* glucosamine (N-acetyl)-6-sulfatase (Sanfilippo disease)(IIID)(GNS), mRNA," [online]. Bethesda, MD [retrieved on Mar. 5, 2009]. Retrieved from the Internet:<URL: http://www.ncbi.nlm.nih.gov/entrez/viewer.fcgi?db=nucleotide&val=42490755>; 7 pgs.

National Center for Biotechnology Information, National Library of Medicine, National Institutes of Health, GenBank Locus NM_002778, Accession No. NM_0002778, Accession No. NM_000169, "*Homo sapiens* glactosidase, alpha (GLA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4504008>, 4 pgs.

National Center for Biotechnology Information, National Library of Medicine, National Institutes of Health, GenBank Locus NM_002778, Accession No. NM_002778, "*Homo sapiens* prosaposin (variant Gaucher disease and variant metachromatic leukodystrophy) (PSAP), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=11386146>, 8 pgs.

National Center for Biotechnology Information, National Library of Medicine, National Institutes of Health, GenBank Locus NM_004315, Accession No. NM_004315, "*Homo sapiens* N-acylsphingosine amidohydrolase (acid ceramidase) 1 (ASAHI), transcript variant 2, mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=30089929>, 5 pgs.

National Center for Biotechnology Information, National Library of Medicine, National Institutes of Health, GenBank Locus NM_004993, Accession No. NM_004993, "*Homo sapiens* Machado-Joseph disease (spinocerebellar ataxia 3, olivopontocerebellar ataxia 3, autosomal dominant, ataxin 3) (MJD), transcript variant 1, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13518018>; 9 pgs.

National Center for Biotechnology Information, National Library of Medicine, National Institutes of Health, GenBank Locus NM_005908, Accession No. NM_005908, "*Homo sapiens* mannosidase, beta A, lyosomal (MANBA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=24797157>; 4 pgs.

National Center for Biotechnology Information, National Library of Medicine, National Institutes of Health, GenBank Locus

(56) References Cited

OTHER PUBLICATIONS

NM_007308, Accession No. NM_007308, "*Homo sapiens* synuclein, alpha (nonA4 component of amyloid precursor) (SNCA), transcript variant NACP112, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=6806897>; 5 pgs.

National Center for Biotechnology Information, National Library of Medicine, National Institutes of Health, GenBank Locus NM_009124, Accession No. NM_009124, "Definition," [online]. Bethesda, MD [retrieved on Mar. 5, 2009]. Retrieved from the Internet:<URL:http://www.ncbi.nim.nih.govientrez/viewerfcgi?db=nucleotide&val=33636695>: 5 pgs.

National Center for Biotechnology Information, National Library of Medicine, National Institutes of Health, GenBank Locus NM_011792, Accession No. NM_011792, Version NM_011792.2, "Mus musculus beta-site APP cleaving enzyme 1 (Bace 1), mRNA," [online]. Bethesda, MD [retrieved on Mar. 5, 2009]. Retrieved from the Internet:<URL:http://www.ncbi.nlm.nih.govientrez/viewer.fcgi?db=nucleotide&val=31981411>; 5 pgs.

National Center for Biotechnology Information, National Library of Medicine, National Institutes of Health, GenBank Locus NM_011792.2, Accession No. NM_011792, "Mus musculus beta-site APP cleaving enzyme (Bace), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=6857758>; 4 pgs.

National Center for Biotechnology Information, National Library of Medicine, National Institutes of Health, GenBank Locus NM_012104, Accession No. NM_012104, "*Homo sapiens* beta-site APP-cleaving enzyme 1 (BACE1), transcript variant a, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255011>; 8 pgs.

National Center for Biotechnology Information, National Library of Medicine, National Institutes of Health, GenBank Locus NM_012104, Accession No. NM_012104, Version NM_012104.2, "*Homo sapiens* beta-site APP-cleaving enzyme (BACE), transcript variant a, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040369>: 10 pgs.

National Center for Biotechnology Information, National Library of Medicine, National Institutes of Health, GenBank Locus NM_013995, Accession No. NM_013995, "*Homo sapiens* lysosomal-associated membrane protein 2 (LAMP2), transcript variant LAMP2B, mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=7669502>: 6 pgs.

National Center for Biotechnology Information, National Library of Medicine, National Institutes of Health, GenBank Locus NM_030660, Accession No. NM_030660, "*Homo sapiens* Machado-Joseph disease (spinocerebellar ataxia 3, olivopontocerebellar ataxia 3, autosomal dominant, ataxin 3) (MJD), transcript variant 2, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13518012>; 8 pgs.

National Center for Biotechnology Information, National Library of Medicine, National Institutes of Health, GenBank Locus NM_032520, Accession No. NM_032520, "*Homo sapiens* N-acetylglucosamine-1-phosphotransferase, gamma subunit (GNPTAG), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=42476109>; 5 pgs.

National Center for Biotechnology Information, National Library of Medicine, National Institutes of Health, GenBank Locus NM_138971, Accession No. NM_138971, "*Homo sapiens* beta-site APP-cleaving enzyme 1 (BACE1), transcript variant c, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255012>; 8 pgs.

National Center for Biotechnology Information, National Library of Medicine, National Institutes of Health, GenBank Locus NM_138971, Accession No. NM_138971, Version NM_138971.1, "*Homo sapiens* beta-site APP-cleaving enzyme (BACE), transcript variant c, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040363>; 10 pgs.

National Center for Biotechnology Information, National Library of Medicine, National Institutes of Health, GenBank Locus NM_138972, Accession No. NM_138972, "*Homo sapiens* beta-site APP-cleaving enzyme 1 (BACE1), transcript variant b, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255013>; 8 pgs.

National Center for Biotechnology Information, National Library of Medicine, National Institutes of Health, GenBank Locus NM_138972, Accession No. NM_138972, Version NM_138972.1, "*Homo sapiens* beta-site APP-cleaving enzyme (BACE), transcript variant b, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040365>; 10 pgs.

National Center for Biotechnology Information, National Library of Medicine, National Institutes of Health, GenBank Locus NM_138973, Accession No. NM_138973, "*Homo sapiens* beta-site APP-cleaving enzyme 1 (BACE1), transcript variant d, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=46255014>; 8 pgs.

National Center for Biotechnology Information, National Library of Medicine, National Institutes of Health, GenBank Locus NM_138973, Accession No. NM_138973, Version NM_138973.1, "*Homo sapiens* beta-site APP-cleaving enzyme (BACE), transcript variant d, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=21040367>; 10 pgs.

National Center for Biotechnology Information, National Library of Medicine, National Institutes of Health, GenBank Locus U24233, Accession No. U24233, "Mus musculus huntingtin (Hd) mRNA, complete cds," [online]. Bethesda, MD [retrieved on Mar. 5, 2009]. Retrieved from the Internet:<URL:http://www.ncbi.nlm.nih.gov/entrez/viewer.fcgi?db=nucleotide&val=902003>; 5 pgs.

National Center for Biotechnology Information, National Library of Medicine, National Institutes of Health, GenBank Locus XM_032588, Accession No. XM_032588, "*Homo sapiens* dentatorubral-pallidoluysian atrophy (artrophin-1) (DRPLA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=20555988>; 3 pgs.

National Center for Biotechnology Information, National Library of Medicine, National Institutes of Health, GenBank .Locus XM_132846, Accession No. XM_132846, "Mus musculus dentatorubral pallidoluysian atrophy (Drpla) mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=20832263>; 3 pgs.

Noonberg et al Nucl. Acid Res. 22(14) 2830-2836 (1994).

Noordmans et al., Soc. Neurosci. Abstr. 27, Program 572.14 (2001).

Ohkawa Nucl. Acid. Symp. Ser. 27, 15-16 (1992).

Ohno et al., "BACEI Deficiency Rescues Memory Deficits and Cholinergic Dysfunction in a Mouse Model of Alzheimer's Disease," Neuron, Jan. 2004; 4I: 27-33.

Ojwang et al., Proc. Nat. Acad. Sci. 89 10802-10806.

Paxinos et al the Mouse Brain in Stereotactic Coordinates, Acad. Press 2nd Ed. (2001).

Potter, N. T. et al., "Technical standards and guidelines for huntington disease testing," Genetics in Medicine 6:61-65 (2004).

Promega Corporation, T4 DNA Ligase Blue/White Cloning Qualified, Part# 9PIM180, Revised Apr. 2005, 2 pgs.

Promega Corporation, T4 DNA Polymerase(a), Part# 9PIM421, Revised May 2004, 2 pgs.

Qiagen, Qiaex II Handbook, Feb. 1999, 24 pgs.

(56) References Cited

OTHER PUBLICATIONS

Qiagen, Rneasy Mini Handbook, 3rd Edition, Jun. 2001, 116 pgs.
R&D Systems, β-Secretase Activity Kit, Catalog No. FP002, Aug. 2002, 2 pgs.
Roberds et al., "BACE knockout mice are healthy despite lacking the primary β-secretase activity in brain: implications for Alzheimer's disease therapeutics," Human Molecular Genetics, Jun. 2001; 10(12): 1317-1324.
Ryu, Biomaterials 26: 319-326 (2005).
Salehi et al., J. Neural Transm. 106 955-986 (1999).
Sapru et al., Annual Meeting Soc. Neurosci. Abstract 297.9, XP001204566 (2003).
Sarver et al., Science 247, 1222-1225 (1990).
Scanlon et al., Proc. Nat. Acad. Sci. 88, 10591-10595 (1995).
Schenk, "Amyloid-β immunotherapy for Alzheimer's disease: the end of the beginning," Nature Reviews—Neuroscience, Oct. 2002; 3: 824-828.
Scherr et al., Cell Cycle 2(3) 251-257 (2003).
Serra et at., Medical Image Analysis 1(4) 317-329 (1996).
Singer et al., Nat. Neurosci. 8(10) 1343-1349 (ePub Aug. 28, 2005).
Stackman et al., Experimental Neurology 184, 510-520 (2003).
Strategene, AAV Helper-Free System, Instruction Manual, Catalog #240071, #240074, #240075, Revision #084007i, Aug. 2004, 50 pgs.
Strategene, pBluescript® II Phagemid Vectors, Instruction Manual, Catalog #212205, #212206, #212207, #212208, Revision #083001m, Aug. 2003, 35 pgs.
Sullenger, Science 262, p. 1566 (Dec. 3, 1993).
Taira et al., Nucl. Acid. Res. 19(19) 5125-5130 (1991).
Thompson et al., Nucl. Acid. Res. 23(12), 2259 (1995).
Timson et al., Biochem J 363:515-520 (2002).
Tuscjl Lab, "The siRNA user guide," Revised May 2004, [online]. Retrieved on Nov. 29, 2005. Retrieved from the Internet: <URL:rockefeller.edu/labheads/tuschl/sirna.html>; 6 pgs.
Ui-Tei et al., "Guidelines for the selection of highly effective siRNA sequences for mammalian and chick RNA interference,"; Nucleic Acids Research (2004); vol. 32, No. 3, pp. 936-948.
Valbonesi et al., Ttransf. And Apheresis Sci. 30: 153-156 (2004).
Van Bilsen et al., "Identification and allele-specific silencing of the mutant huntingtin allele in Huntington's disease patient-derived fibroblasts," Human Gene Therapy, vol. 19, pp. 710-718 (2008).
Vassar et al., Science 286 735-741 (1999).
Ventura et al., Nucl. Acid. Res. 21(14) 3249-3255 (1993).
Vickers, Journal of Bio. Chemistry, vol. 278, No. 9 7108-7118 (2003).
Watanabe et al., J. Mol. Cel. Card. 37 (3) 691-698 (2004).
Weerasinghe et al., J. Virol. 65(10), 5531-3334 (1991).
Whitesell et al., Proc. Nat. Acad. Sci. 90: 4665-4669 (1993).
Xia et al., Nat. Biotech. 20, 1006-1010 (2002).
Xia et al., Nat. Med. 10(8) 816-820 (2004).
Yamamoto et al., Cell 101, 57-66 (2000).
Yu et al., Proc. Nat. Acad. Sci. 90 6340-6344 (1993).
Yu et al., Proc. Nat. Acad. Sci. 99 6047-6052 (2002).
Zhang et al., "Global Non-Viral Gene Transfer to the Primate Brain Following Intravenous Administration," Molecular Therapy, Jan. 2003; 7(1): 11-18.
Zhang et al., "In vivo knockdown of gene expression in brain cancer with intravenous RNAi in adult rats," J. Gene Med., 2003; 5:1039-1045; published online Aug. 4, 2003.
Zhang et al., "Intravenous RNA Interference Gene Therapy Targeting the Human Epidermal Growth Factor Receptor Prolongs Survival in Intracranial Brain Cancer," Clinical Cancer Research, Jun. 1, 2004; 10:3667-3677.
Zhang et al., 1996 J. Mol. Neurosci. 7: 13-28 (1996).
Zhao et al., J. Biol. Chem. 271(49), 31407-31411 (Dec. 1996).
Zlokovic et al., Neurosurgery 40 805-813 (1997).
Tjelle et al., "Taking Electroporation-Based Delivery of DNA Vaccination into Humans: A Generic Clinical Protocol,"; Methods in Molecular Biology, vol. 423, Chap. 39, pp. 497-507.
Ambion, Inc., SiPORT siRNA Electrospun Buffer (Part No. AM8990G, AM8990, AM8991) Protocol (18 pgs.).

Warby et al, CAG Expansion in the Huntington Disease Gene is Assoicated wiht a Speicfic and Tagetable Predisposing Haplogroup; Am. J. of Human Genetics, Mar. 13, 2009, pates 351-355; vol. 84.
Akey et al., "The effect that genotyping errors have on the robustness of common linkage-disequilibrium measures," Am. J. Hum. Genet. (2001); 68: pp. 1447-1456.
Albert et al, "Light-directed 5'→3' synthesis of complex oligonucleotide microarrays," Nucleic Acids Research (2003); vol. 31, No. 7: pp. 1-9.
Baner et al., "Parallel gene analysis with allele-specific padlock probes and tag microarrays," Nucleic Acids Research (2003); vol. 31, No. 7: pp. 1-7.
Beaudet et al., "Homogeneous assays for single-nucleotide polymorphism typing using alphascreen," Genome Research (2000); 11: pp. 600-608.
Bergen et al., "Effects of DNA mass on multiple displacement whole genome amplification and genotyping performance," BMC Biotechnology (2005); 5:24: pp. 1-11.
Booth et al., "Application of DNA array technology for diagnostic microbiology," Can. J. Infect. Dis. (Nov./Dec. 2000); vol. 11, No. 6: pp. 291-294.
Bordoni et al., "Investigation of the multiple anchors approach in oligonucleotide microarray preparation using linear and stem-loop structured probes," Nucleic Acids Research (2002); vol. 30, No. 8: pp. 1-7.
Christensen et al., "The association between genetic variants in hMLH1 and hMSH2 and the development of sporadic colorectal cancer in the Danish population," BMC Medical Genetics (2008); 9:52: pp. 1-13.
"Current Awareness on Comparative and Functional Genomics," Comp. Func. Genom. (2001); 2: pp. 49-56.
Cozza et al., "TAMGeS: a three-array method for genotyping of SNPSs by a dual-colour approach," BMC Genomics (2007); 8:10: pp. 1-14.
Erdogan et al., "Detection of mitochrondrial single nucleotide polymorphisms using a primer elongation reaction on oligonucleotide microarrays," Nucleic Acids Research (2001); vol. 29, No. 7: pp. 1-7.
Flavell et al., "A microarray-based high throughput molecular marker genotyping method: the tagged microarray marker (TAM) approach," Nucleic Acids Research (2003), vol. 31, No. 19: pp. 1-8.
Forche et al., "Demonstration of loss of heterozygosity by single-nucleotide polymorphism microarray analysis and alterations in strain morphology in candida albicans strains during infection," Eukaryotic Cell (Jan. 2005); vol. 4, No. 1: pp. 156-165.
Forche et al., "Genome-wide single-nucleotide polymorphism map for candida albicans," Eukaryotic Cell (Jun. 2004); vol. 3, No. 3: pp. 705-714.
Fredriksson et al., "Multiplex amplification of all coding sequences within 10 cancer genes by gene-collector," Nucleic Acids Research (2007); vol. 35, No. 7: pp. 1-6.
Gunderson et al., "Decoding randomly ordered DNA arrays," Genome Research (2004); 14: pp. 870-877.
Hansen et al., "Quantitative evaluation of oligonucleotide surface concentrations using polymerization-based amplification," Anal Bioanal Chem (2008); 392: pp. 167-175.
Hayden et al., "Multiplex-Ready PCR: a new method for multiplexed SSR and SNP genotyping," BMC Genomics (2008) 9:80, pp. 1-12.
Hirschhorn et al., "SBE-TAGS: an array-based method for efficient single-nucleotide polymorphism genotyping," PNAS (Oct. 24, 2000); vol. 97, No. 22: pp. 12164-12169.
Hoskins et al., "Single nucleotide polymorphism markers for genetic mapping in *Drosophila melanogaster*," Genome Research (2001); 11: pp. 1100-1113.
Hu et al., "A highly sensitive and specific system for lare-scale gene expression profiling, " BMC Genomics (2008); 9:9, pp. 1-14.
Hu et al., "Accutyping: new algorithms for automated analysis of data from high-throughput genotyping with oligonucleotide microarrays," Nucleic Acids Research (2006); vol. 34, No. 17: pp. 1-8.
Hultin et al., "Competitive enzymatic reaction to conrol allele-specific extensions," Nucleic Acids Research (2005) vol. 33, No. 5: pp. 1-10.

(56) References Cited

OTHER PUBLICATIONS

Kinoshita et al., "Multiple primer extension by DNA polymerase on a novel plastic DNA array coated with a biocompatible polymer," Nucleic Acids Research (2007); vol. 35, No. 1: pp. 1-9.
Kirk et al., "Single nucleotide polymorphism seeking long term association with complex disease," Nucleic Acids Research (2002); vol. 30, No. 15: pp. 3295-3311.
Komulainen et al., "Risk alleles of USF1 gene predict cardiovascular disease of women in two prospective studies," PLoS Genetics (May 2006); vol. 2, No. 5: pp. -0672-0681.
Le Berre et al., "Dendrimeric coating of glass slides for sensitive DNA microarrays analysis," Nucleic Acids Research (2003); vol. 31, No. 16: pp. 1-8.
Liljedahl et al., "Detecting imbalanced expression of SNP alleles by minisequencing on microarrays," BMC Biotechnology (2004); 4:24: pp. 1-10.
Lindroos et al., "Multiplex SNP genotyping in pooled DNA samples by a four-colour microarray system," Nucleic Acids Research (2002); vol. 30, No. 14: pp. 2-9.
Lindroos et al., "Minisequencing on oligonucleotide microarrays: comparison of immobilisation chemistries," Nucleic Acids Research (2001); vol. 29, No. 13: pp. 1-7.
Lovmar et al., "Silhouette scores for assessment of SNP genotype clusters," BMC Genomics (2005); 6:35: pp. 1-6.
Lovmar et al., "Quantitative evaluation by minisequencing and microarrays reveals accurate multiplexed SNP genotyping of whole genome amplified DNA," Nucleic Acids Research (2003); vol. 31, No. 21: pp. 1-9.
Lovmar et al., "Microarrays for genotyping human group a rotavirus by multiplex capture and type-specific primer extension," Journal of Clinical Microbiology (Nov. 2003); vol. 41, No. 11: pp. 5153-5158.
Macdonald et al., "A low-cost open-source SNP genotyping platform for association mapping applications," Genome Biology (2005); 6:R105.
Martin et al., "A rapid method to map mutations in *Droso-phila*," Genome Biology (2001); 2(9): research0036.1.
Mitterer et al., "Microarray-based identification of bacteria in clinical samples by solid-phase PCR amplification of 23S ribosomal DNA sequences," Journal of Clinical Microbiology (Mar. 2004); vol. 42, No. 3: pp. 1048-1057.
O'Meara et al., "SNP typing by apyrase-mediated allele-specific primer extension on DNA microarrays," Nucleic Acids Research (2002); vol. 30, No. 15: pp. 1-8.
Pastinen et al., "A system for specific, high-throughput genotyping by allele-specific primer extension on microarrays," Genome Research (2000); 10:1031-1042.
Pincas et al., "High sensitivity endoV mutation scanning through real-time ligase proofreading," Nucleic Acids Research (2004); vol. 32, No. 19: pp. 1-13.
Podder et al., "Robust SNP genotyping by multiplex PCR and arrayed primer extension," BMC Medical Genomics (2008); 1:5: pp. 1-15.
Raitio et al., "Y-chromosomal SNPs in finno-ugric-speaking populations analyzed by minisequencing on microarrays," Genome Research (2001); 11:471-482.
Saarela et al., "PRKCA and multiple sclerosis: association in two independent populations," PLoS Genetics (Mar. 2006); vol. 2, No. 3: pp. 0364-0375.
Saetre et al., "Sex chromosome evolution and speciation in ficedula flycatchers," Pro. R. Soc. Lond. B (2003); 270, 53-59.
Sibley et al., "Genetic approaches to studyign virulence and pathogenesis in toxoplasma gondii," Phil. Trans. R. Soc. Lond. B (2002); 357, 81-88.
Stengel et al., "Surface plasmon field-enhanced fluorescence spectroscopy studies of primer extension reactions," Nucleic Acids Research (2005); vol. 33, No. 7: pp. 1-10.
Volokhov et al., "identification of listeria species by microarray-based assay," Journal of Clinical Microbiology (Dec. 2002); vol. 40, No. 12: pp. 4720-4728.
Wakai et al., "A novel method of idnetifying genetic mutations using an electrochemical DNA array," Nucleic Acids Research (2004); vol. 32, No. 18: pp. 1-10.
Wang et al., "A genotyping system capable of simultaneously analyzing >1000 single nucleotide polymorpisms in a haploid genome," Genome Research (2005); 15:276-283.
Xu et al., "Multiplexed SNP genotyping using the Qbead(TM) system: a quantum dot-encoded microsphere-based assay," Nucleic Acids Research (2003); vol. 31, No. 8: pp. 1-10.
Zhong et al., "Single-nucleotide polymorphism genotyping on optical thin-film biosensor chips," PNAS (2003); vol. 100, No. 20: pp. 11559-11564.
NEB Catalog (1998/1999), pp. 121, 284.
Ahern (The Scientist, vol. 9, No. 15, p. 20, Jul. 1995).
Office Action issued on Sep. 27, 2010 for U.S. Appl. No. 11/439,858.
Office Action issued on Jun. 21, 2010 for U.S. Appl. No. 11/439,858.
Office Action issued on Jun. 26, 2009 for U.S. Appl. No. 11/439,858.
Office Action issued Jan. 15, 2009 for U.S. Appl. No. 11/439,858.
Roche Molecular Biochemicals, "PCR Applications Manual," pp. 95, 98-100, 102 (2nd Edition) (1999).
Eun et al., "Molecular beacons: a new approach to plant virus detection"; Phytopathology (Mar. 2000): vol. 90, No. 3, pp. 269-275.
Database SNP (online) (Sep. 13, 2000) XP002522351, retrieved from NCBI Database Accession No. ss1556778, ref. SNP rs363099.
Database SNP (online) (Aug. 20, 2004) XP002522352, retrieved from NCBI Database Accession No. ss23893221, ref. SNP rs363099.
Database SNP (online) (Sep. 6, 2000) XP002522353, retrieved from NCBI Database Accession No. ss1303522, ref. SNP rs362331.

* cited by examiner

A

Forward primer:  5'-CCTTCTCTCCGTATTTAATCTCCTGTA-3'
Reverse primer:  5'-TCATTTCCACCTTCAGCTGTTTGTAA-3'

Target strand sequence:       5'...TCTTCTAGCGTTGAAATACTGTCCCCATCTC...3'
Molecular beacon sequence:            GATCGCAACTTTATGACAGGG -tgcgtga-FAM-5'
                              3'-BHQ1-acgca-

B

Forward primer:  5'-AGATATTGTTCTTTCTCGTATTCAGG-3'
Reverse primer:  5'-TGCTCACTCATTTCCACCTTC-3'

Target strand sequence:       5'...TCTTCTAGCGTTGAACTACTGTCCCCATCTC...3'
Molecular beacon sequence:            AGATCGCAACTTGATGACAGGGGTAG -cugccgc-FAM-5'
                              3'-BHQ1-gccggc-

Fig. 3

SEQUENCE LISTING

<160> NUMBER OF SEQ ID NOS: 97

<210> SEQ ID NO 1
<211> LENGTH: 9
<212> TYPE: DNA
<213> ORGANISM: Homo sapiens

<400> SEQUENCE: 1 aagcctaag                                                           9

<210> SEQ ID NO 2
<211> LENGTH: 10
<212> TYPE: DNA
<213> ORGANISM: Homo sapiens

<400> SEQUENCE: 2
taagcctaag                                                          10

<210> SEQ ID NO 3
<211> LENGTH: 11
<212> TYPE: DNA
<213> ORGANISM: Homo sapiens

<400> SEQUENCE: 3
gtaagcctaa g                                                        11

```
<210> SEQ ID NO 4
<211> LENGTH: 12
<212> TYPE: DNA
<213> ORGANISM: Homo sapiens

<400> SEQUENCE: 4
agtaagccta ag                                                              12

<210> SEQ ID NO 5
<211> LENGTH: 13
<212> TYPE: DNA
<213> ORGANISM: Homo sapiens

<400> SEQUENCE: 5
gagtaagcct aag                                                             13

<210> SEQ ID NO 6
<211> LENGTH: 14
<212> TYPE: DNA
<213> ORGANISM: Homo sapiens

<400> SEQUENCE: 6
cgagtaagcc taag                                                            14

<210> SEQ ID NO 7
<211> LENGTH: 15
<212> TYPE: DNA
<213> ORGANISM: Homo sapiens

<400> SEQUENCE: 7
acgagtaagc ctaag                                                           15

<210> SEQ ID NO 8
<211> LENGTH: 16
<212> TYPE: DNA
<213> ORGANISM: Homo sapiens

<400> SEQUENCE: 8
aacgagtaag cctaag                                                          16

<210> SEQ ID NO 9
<211> LENGTH: 17
<212> TYPE: DNA
<213> ORGANISM: Homo sapiens

<400> SEQUENCE: 9
gaacgagtaa gcctaag                                                         17

<210> SEQ ID NO 10
<211> LENGTH: 18
<212> TYPE: DNA
<213> ORGANISM: Homo sapiens

<400> SEQUENCE: 10
ggaacgagta agcctaag                                                        18

<210> SEQ ID NO 11
<211> LENGTH: 9
<212> TYPE: DNA
<213> ORGANISM: Homo sapiens

<400> SEQUENCE: 11 aagcctaac                                                                   9
```

```
<210> SEQ ID NO 12
<211> LENGTH: 10
<212> TYPE: DNA
<213> ORGANISM: Homo sapiens

<400> SEQUENCE: 12
taagcctaac                                                          10

<210> SEQ ID NO 13
<211> LENGTH: 11
<212> TYPE: DNA
<213> ORGANISM: Homo sapiens

<400> SEQUENCE: 13
gtaagcctaa c                                                        11

<210> SEQ ID NO 14
<211> LENGTH: 12
<212> TYPE: DNA
<213> ORGANISM: Homo sapiens

<400> SEQUENCE: 14
agtaagccta ac                                                       12

<210> SEQ ID NO 15
<211> LENGTH: 13
<212> TYPE: DNA
<213> ORGANISM: Homo sapiens

<400> SEQUENCE: 15
gagtaagcct aac                                                      13

<210> SEQ ID NO 16
<211> LENGTH: 14
<212> TYPE: DNA
<213> ORGANISM: Homo sapiens

<400> SEQUENCE: 16
cgagtaagcc taac                                                     14

<210> SEQ ID NO 17
<211> LENGTH: 15
<212> TYPE: DNA
<213> ORGANISM: Homo sapiens

<400> SEQUENCE: 17
acgagtaagc ctaac                                                    15

<210> SEQ ID NO 18
<211> LENGTH: 16
<212> TYPE: DNA
<213> ORGANISM: Homo sapiens

<400> SEQUENCE: 18
aacgagtaag cctaac                                                   16

<210> SEQ ID NO 19
<211> LENGTH: 17
<212> TYPE: DNA
<213> ORGANISM: Homo sapiens

<400> SEQUENCE: 19
gaacgagtaa gcctaac                                                  17
```

<210> SEQ ID NO 20
<211> LENGTH: 18
<212> TYPE: DNA
<213> ORGANISM: Homo sapiens

<400> SEQUENCE: 20
ggaacgagta agcctaac                                                 18

<210> SEQ ID NO 21
<211> LENGTH: 9
<212> TYPE: DNA
<213> ORGANISM: Homo sapiens

<400> SEQUENCE: 21 gctgagcgg                                                            9

<210> SEQ ID NO 22
<211> LENGTH: 10
<212> TYPE: DNA
<213> ORGANISM: Homo sapiens

<400> SEQUENCE: 22
ggctgagcgg                                                          10

<210> SEQ ID NO 23
<211> LENGTH: 11
<212> TYPE: DNA
<213> ORGANISM: Homo sapiens

<400> SEQUENCE: 23
aggctgagcg g                                                        11

<210> SEQ ID NO 24
<211> LENGTH: 12
<212> TYPE: DNA
<213> ORGANISM: Homo sapiens

<400> SEQUENCE: 24
aaggctgagc gg                                                       12

<210> SEQ ID NO 25
<211> LENGTH: 13
<212> TYPE: DNA
<213> ORGANISM: Homo sapiens

<400> SEQUENCE: 25
caaggctgag cgg                                                      13

<210> SEQ ID NO 26
<211> LENGTH: 14
<212> TYPE: DNA
<213> ORGANISM: Homo sapiens

<400> SEQUENCE: 26
ccaaggctga gcgg                                                     14

<210> SEQ ID NO 27
<211> LENGTH: 15
<212> TYPE: DNA
<213> ORGANISM: Homo sapiens

<400> SEQUENCE: 27

```
tccaaggctg agcgg                                                      15

<210> SEQ ID NO 28
<211> LENGTH: 16
<212> TYPE: DNA
<213> ORGANISM: Homo sapiens

<400> SEQUENCE: 28
atccaaggct gagcgg                                                     16

<210> SEQ ID NO 29
<211> LENGTH: 17
<212> TYPE: DNA
<213> ORGANISM: Homo sapiens

<400> SEQUENCE: 29
catccaaggc tgagcgg                                                    17

<210> SEQ ID NO 30
<211> LENGTH: 18
<212> TYPE: DNA
<213> ORGANISM: Homo sapiens

<400> SEQUENCE: 30
acatccaagg ctgagcgg                                                   18

<210> SEQ ID NO 31
<211> LENGTH: 9
<212> TYPE: DNA
<213> ORGANISM: Homo sapiens

<400> SEQUENCE: 31 gctgagcga                                                              9

<210> SEQ ID NO 32
<211> LENGTH: 10
<212> TYPE: DNA
<213> ORGANISM: Homo sapiens

<400> SEQUENCE: 32
ggctgagcga                                                            10

<210> SEQ ID NO 33
<211> LENGTH: 11
<212> TYPE: DNA
<213> ORGANISM: Homo sapiens

<400> SEQUENCE: 33
aggctgagcg a                                                          11

<210> SEQ ID NO 34
<211> LENGTH: 12
<212> TYPE: DNA
<213> ORGANISM: Homo sapiens

<400> SEQUENCE: 34
aaggctgagc ga                                                         12

<210> SEQ ID NO 35
<211> LENGTH: 13
<212> TYPE: DNA
<213> ORGANISM: Homo sapiens

<400> SEQUENCE: 35
```

```
caaggctgag cga                                              13

<210> SEQ ID NO 36
<211> LENGTH: 14
<212> TYPE: DNA
<213> ORGANISM: Homo sapiens

<400> SEQUENCE: 36
ccaaggctga gcga                                             14

<210> SEQ ID NO 37
<211> LENGTH: 15
<212> TYPE: DNA
<213> ORGANISM: Homo sapiens

<400> SEQUENCE: 37
tccaaggctg agcga                                            15

<210> SEQ ID NO 38
<211> LENGTH: 16
<212> TYPE: DNA
<213> ORGANISM: Homo sapiens

<400> SEQUENCE: 38
atccaaggct gagcga                                           16

<210> SEQ ID NO 39
<211> LENGTH: 17
<212> TYPE: DNA
<213> ORGANISM: Homo sapiens

<400> SEQUENCE: 39
catccaaggc tgagcga                                          17

<210> SEQ ID NO 40
<211> LENGTH: 18
<212> TYPE: DNA
<213> ORGANISM: Homo sapiens

<400> SEQUENCE: 40
acatccaagg ctgagcga                                         18

<210> SEQ ID NO 41
<211> LENGTH: 9
<212> TYPE: DNA
<213> ORGANISM: Homo sapiens

<400> SEQUENCE: 41 gcgttgaat                                                    9

<210> SEQ ID NO 42
<211> LENGTH: 10
<212> TYPE: DNA
<213> ORGANISM: Homo sapiens

<400> SEQUENCE: 42
agcgttgaat                                                  10

<210> SEQ ID NO 43
<211> LENGTH: 11
<212> TYPE: DNA
<213> ORGANISM: Homo sapiens
```

```
<400> SEQUENCE: 43
tagcgttgaa t                                                       11

<210> SEQ ID NO 44
<211> LENGTH: 12
<212> TYPE: DNA
<213> ORGANISM: Homo sapiens

<400> SEQUENCE: 44
ctagcgttga at                                                      12

<210> SEQ ID NO 45
<211> LENGTH: 13
<212> TYPE: DNA
<213> ORGANISM: Homo sapiens

<400> SEQUENCE: 45
tctagcgttg aat                                                     13

<210> SEQ ID NO 46
<211> LENGTH: 14
<212> TYPE: DNA
<213> ORGANISM: Homo sapiens

<400> SEQUENCE: 46
ttctagcgtt gaat                                                    14

<210> SEQ ID NO 47
<211> LENGTH: 15
<212> TYPE: DNA
<213> ORGANISM: Homo sapiens

<400> SEQUENCE: 47
cttctagcgt tgaat                                                   15

<210> SEQ ID NO 48
<211> LENGTH: 16
<212> TYPE: DNA
<213> ORGANISM: Homo sapiens

<400> SEQUENCE: 48
tcttctagcg ttgaat                                                  16

<210> SEQ ID NO 49
<211> LENGTH: 17
<212> TYPE: DNA
<213> ORGANISM: Homo sapiens

<400> SEQUENCE: 49
ttcttctagc gttgaat                                                 17

<210> SEQ ID NO 50
<211> LENGTH: 18
<212> TYPE: DNA
<213> ORGANISM: Homo sapiens

<400> SEQUENCE: 50
gttcttctag cgttgaat                                                18

<210> SEQ ID NO 51
<211> LENGTH: 19
<212> TYPE: DNA
<213> ORGANISM: Homo sapiens
```

```
<400> SEQUENCE: 51
tgttcttcta gcgttgaat                                              19

<210> SEQ ID NO 52
<211> LENGTH: 20
<212> TYPE: DNA
<213> ORGANISM: Homo sapiens

<400> SEQUENCE: 52
gtgttcttct agcgttgaat                                             20

<210> SEQ ID NO 53
<211> LENGTH: 9
<212> TYPE: DNA
<213> ORGANISM: Homo sapiens

<400> SEQUENCE: 53 gcgttgaag                                                          9

<210> SEQ ID NO 54
<211> LENGTH: 10
<212> TYPE: DNA
<213> ORGANISM: Homo sapiens

<400> SEQUENCE: 54
agcgttgaag                                                        10

<210> SEQ ID NO 55
<211> LENGTH: 11
<212> TYPE: DNA
<213> ORGANISM: Homo sapiens

<400> SEQUENCE: 55
tagcgttgaa g                                                      11

<210> SEQ ID NO 56
<211> LENGTH: 12
<212> TYPE: DNA
<213> ORGANISM: Homo sapiens

<400> SEQUENCE: 56
ctagcgttga ag                                                     12

<210> SEQ ID NO 57
<211> LENGTH: 13
<212> TYPE: DNA
<213> ORGANISM: Homo sapiens

<400> SEQUENCE: 57
tctagcgttg aag                                                    13

<210> SEQ ID NO 58
<211> LENGTH: 14
<212> TYPE: DNA
<213> ORGANISM: Homo sapiens

<400> SEQUENCE: 58
ttctagcgtt gaag                                                   14

<210> SEQ ID NO 59
<211> LENGTH: 15
<212> TYPE: DNA
```

```
<213> ORGANISM: Homo sapiens

<400> SEQUENCE: 59
cttctagcgt tgaag                                                    15

<210> SEQ ID NO 60
<211> LENGTH: 16
<212> TYPE: DNA
<213> ORGANISM: Homo sapiens

<400> SEQUENCE: 60
tcttctagcg ttgaag                                                   16

<210> SEQ ID NO 61
<211> LENGTH: 17
<212> TYPE: DNA
<213> ORGANISM: Homo sapiens

<400> SEQUENCE: 61
ttcttctagc gttgaag                                                  17

<210> SEQ ID NO 62
<211> LENGTH: 18
<212> TYPE: DNA
<213> ORGANISM: Homo sapiens

<400> SEQUENCE: 62
gttcttctag cgttgaag                                                 18

<210> SEQ ID NO 63
<211> LENGTH: 19
<212> TYPE: DNA
<213> ORGANISM: Homo sapiens

<400> SEQUENCE: 63
tgttcttcta gcgttgaag                                                19

<210> SEQ ID NO 64
<211> LENGTH: 20
<212> TYPE: DNA
<213> ORGANISM: Homo sapiens

<400> SEQUENCE: 64
gtgttcttct agcgttgaag                                               20

<210> SEQ ID NO 65
<211> LENGTH: 9
<212> TYPE: DNA
<213> ORGANISM: Homo sapiens

<400> SEQUENCE: 65 cacacagtg                                                            9

<210> SEQ ID NO 66
<211> LENGTH: 10
<212> TYPE: DNA
<213> ORGANISM: Homo sapiens

<400> SEQUENCE: 66
gcacacagtg                                                          10

<210> SEQ ID NO 67
<211> LENGTH: 11
```

```
<212> TYPE: DNA
<213> ORGANISM: Homo sapiens

<400> SEQUENCE: 67
tgcacacagt g                                                        11

<210> SEQ ID NO 68
<211> LENGTH: 12
<212> TYPE: DNA
<213> ORGANISM: Homo sapiens

<400> SEQUENCE: 68
gtgcacacag tg                                                       12

<210> SEQ ID NO 69
<211> LENGTH: 13
<212> TYPE: DNA
<213> ORGANISM: Homo sapiens

<400> SEQUENCE: 69
agtgcacaca gtg                                                      13

<210> SEQ ID NO 70
<211> LENGTH: 14
<212> TYPE: DNA
<213> ORGANISM: Homo sapiens

<400> SEQUENCE: 70
aagtgcacac agtg                                                     14

<210> SEQ ID NO 71
<211> LENGTH: 15
<212> TYPE: DNA
<213> ORGANISM: Homo sapiens

<400> SEQUENCE: 71
gaagtgcaca cagtg                                                    15

<210> SEQ ID NO 72
<211> LENGTH: 16
<212> TYPE: DNA
<213> ORGANISM: Homo sapiens

<400> SEQUENCE: 72
tgaagtgcac acagtg                                                   16

<210> SEQ ID NO 73
<211> LENGTH: 17
<212> TYPE: DNA
<213> ORGANISM: Homo sapiens

<400> SEQUENCE: 73
atgaagtgca cacagtg                                                  17

<210> SEQ ID NO 74
<211> LENGTH: 18
<212> TYPE: DNA
<213> ORGANISM: Homo sapiens

<400> SEQUENCE: 74
gatgaagtgc acacagtg                                                 18

<210> SEQ ID NO 75
```

```
<211> LENGTH: 9
<212> TYPE: DNA
<213> ORGANISM: Homo sapiens

<400> SEQUENCE: 75 cacacagta                                                                  9

<210> SEQ ID NO 76
<211> LENGTH: 10
<212> TYPE: DNA
<213> ORGANISM: Homo sapiens

<400> SEQUENCE: 76
gcacacagta                                                                10

<210> SEQ ID NO 77
<211> LENGTH: 11
<212> TYPE: DNA
<213> ORGANISM: Homo sapiens

<400> SEQUENCE: 77
tgcacacagt a                                                              11

<210> SEQ ID NO 78
<211> LENGTH: 12
<212> TYPE: DNA
<213> ORGANISM: Homo sapiens

<400> SEQUENCE: 78
gtgcacacag ta                                                             12

<210> SEQ ID NO 79
<211> LENGTH: 13
<212> TYPE: DNA
<213> ORGANISM: Homo sapiens

<400> SEQUENCE: 79
agtgcacaca gta                                                            13

<210> SEQ ID NO 80
<211> LENGTH: 14
<212> TYPE: DNA
<213> ORGANISM: Homo sapiens

<400> SEQUENCE: 80
aagtgcacac agta                                                           14

<210> SEQ ID NO 81
<211> LENGTH: 15
<212> TYPE: DNA
<213> ORGANISM: Homo sapiens

<400> SEQUENCE: 81
gaagtgcaca cagta                                                          15

<210> SEQ ID NO 82
<211> LENGTH: 16
<212> TYPE: DNA
<213> ORGANISM: Homo sapiens

<400> SEQUENCE: 82
tgaagtgcac acagta                                                         16
```

```
<210> SEQ ID NO 83
<211> LENGTH: 17
<212> TYPE: DNA
<213> ORGANISM: Homo sapiens

<400> SEQUENCE: 83
atgaagtgca cacagta                                                  17

<210> SEQ ID NO 84
<211> LENGTH: 18
<212> TYPE: DNA
<213> ORGANISM: Homo sapiens

<400> SEQUENCE: 84
gatgaagtgc acacagta                                                 18

<210> SEQ ID NO 85
<211> LENGTH: 19
<212> TYPE: DNA
<213> ORGANISM: Homo sapiens

<400> SEQUENCE: 85
gccttcgagt ccctcaagt                                                19

<210> SEQ ID NO 86
<211> LENGTH: 20
<212> TYPE: DNA
<213> ORGANISM: Homo sapiens

<400> SEQUENCE: 86
gacaatgatt cacacggtct                                               20

<210> SEQ ID NO 87
<211> LENGTH: 20
<212> TYPE: DNA
<213> ORGANISM: Homo sapiens

<400> SEQUENCE: 87
ctcgcctcca gcatgaaagt                                               20

<210> SEQ ID NO 88
<211> LENGTH: 18
<212> TYPE: DNA
<213> ORGANISM: Homo sapiens

<400> SEQUENCE: 88
gtgactgggg cattgatt                                                 18

<210> SEQ ID NO 89
<211> LENGTH: 35
<212> TYPE: DNA
<213> ORGANISM: Homo sapiens

<400> SEQUENCE: 89
tcacgcagat cgcaacttaa tgacagggtg cgtga                              35

<210> SEQ ID NO 90
<211> LENGTH: 40
<212> TYPE: DNA
<213> ORGANISM: Homo sapiens

<400> SEQUENCE: 90
gcgctagaga tcgcaacttc atgacagggg tagctagcgc                         40
```

```
<210> SEQ ID NO 91
<211> LENGTH: 27
<212> TYPE: DNA
<213> ORGANISM: Homo sapiens

<400> SEQUENCE: 91
ccttctctcc gtatttaatc tcctgta                                              27

<210> SEQ ID NO 92
<211> LENGTH: 27
<212> TYPE: DNA
<213> ORGANISM: Homo sapiens

<400> SEQUENCE: 92
tcatttccac cttcagctgt tttgtaa                                              27

<210> SEQ ID NO 93
<211> LENGTH: 26
<212> TYPE: DNA
<213> ORGANISM: Homo sapiens

<400> SEQUENCE: 93
agatattgtt ctttctcgta ttcagg                                               26

<210> SEQ ID NO 94
<211> LENGTH: 21
<212> TYPE: DNA
<213> ORGANISM: Homo sapiens

<400> SEQUENCE: 94
tgctcactca tttccacctt c                                                    21

<210> SEQ ID NO 95
<211> LENGTH: 19
<212> TYPE: DNA
<213> ORGANISM: Homo sapiens

<400> SEQUENCE: 95
actcctccac ctttgacgc                                                       19

<210> SEQ ID NO 96
<211> LENGTH: 21
<212> TYPE: DNA
<213> ORGANISM: Homo sapiens

<400> SEQUENCE: 96
gttgctgtag ccaaattcgt t                                                    21

<210> SEQ ID NO 97
<211> LENGTH: 21
<212> TYPE: DNA
<213> ORGANISM: Artificial
<220> FEATURE:
<223> OTHER INFORMATION: siRNA sequence

<400> SEQUENCE: 97
gaaguacugu ccccaucuct t                                                    21
```

METHODS AND KITS FOR LINKING POLYMORPHIC SEQUENCES TO EXPANDED REPEAT MUTATIONS

CROSS REFERENCE TO RELATED APPLICATION(S)

This application is a continuation-in-part and claims the benefit of U.S. patent application Ser. No. 11/439,858, filed on May 24, 2006, the entire teachings of which are incorporated herein by reference.

FIELD OF THE INVENTION

The present invention relates generally to compositions and methods for diagnosing diseases which have an allele-specific therapy and a disease-causing mutation that is sufficiently distant from the molecular site of the therapy to require a diagnostic linking method.

BACKGROUND OF THE INVENTION

Expansions of CAG trinucleotide repeats (CAG repeats) in coding regions of human genes cause numerous disorders by generating proteins with elongated polyglutamine (polyQ) stretches. This group of disorders includes by way of example Dystophia myotonica, Spinocerebellar ataxia type 1, Spinocerebellar ataxia type 2, Spinocerebellar ataxia type 3, Spinocerebellar ataxia type 6, Spinocerebellar ataxia type 7, Spinocerebellar ataxia type 8, Spinocerebellar ataxia type 17, Huntington disease-like 2, Spinal and bulbar muscular atrophy, Huntington disease, Dentatorubral-pallidoluysian atrophy, Oculopharyngeal dystrophy, Congenital central hypoventilation syndrome, Infantile spasms, Synpolydactyl), Cleidocranial dysplasia, Holoprosencephaly, Hand-foot-genital syndrome, Type II blephorophimosis, ptosis, and epicanthus inversus syndrome. (Wanker E. E. (2000) *Biol. Chem.*, 381:937-942; Gusella J. F. and MacDonald, M. E. (2000) *Nature Rev. Neurosci.*, 1:109-115; and Usdin K. and Grabczyk, E. (2000) *Cell. Mol. Life. Sci.*, 57:914-931).

For purposes of illustration only Huntington's disease (HD) will be discussed herein. HD is a chronic neurodegenerative disorder which is inherited as an autosomal dominant trait and is characterized by chorea, dementia and personality disorder. Martin, J. B. and Gusella, J. F. (1986) *N. Engl. J. Med.* 315:1267-1276. The gene responsible for HD contains an expanded and unstable CAG trinucleotide repeat. Huntington's Disease Collaborative Research Group (1993) *Cell* 72:971-983.

The HD gene (IT15 gene), which encodes huntingtin, a 350 kDa protein of unknown function, is located on the human chromosome 4 and consists of 67 exons. The disease-causing mutation is a CAG repeat expansion located within exon 1 of the HD gene (HD exon1). The CAG repeat is translated into a polyQ stretch. The disease manifests itself when the polyQ stretch exceeds the critical length of 37 glutamines (pathological threshold), whereas 8-35 glutamine residues in huntingtin are tolerated by neuronal cells. Experimental evidence has been presented that huntingtin fragments with polyQ tracts in the pathological range (more than 37 glutamines), but not in the normal range (20-32 glutamines), form high molecular weight protein aggregates with a fibrillar morphology in vitro and in cell culture model systems (Scherzinger et al. (1999) *Proc. Natl. Acad. Sci. USA*, 96:4604-4609; and Waelter et al., (2001) *Mol. Biol. Cell*, 12:1393-1407). In addition, inclusions with aggregated N-terminally truncated huntingtin protein were detected in HD transgenic mice carrying a CAG repeat expansion of 115-156 units and in HD patient brains (Davies et al., (1997) *Cell*, 90:537-548; and DiFiglia et al., (1997) *Science*, 277:1990-1993), suggesting that the process of aggregate formation may be important for the progression of HD. The mechanisms, however, by which the elongated polyQ sequences in huntingtin cause dysfunction and neurodegeneration are not yet understood (Scherzinger et al., (1999); Tobin A. J. and Signer, E. R. (2000) *Trends Cell Biol.*, 10:531-536; and Perutz M. F. (1999) Glutamine repeats and neurodegenerative diseases: molecular aspects. *Trends Biochem. Sci.*, 24:58-63).

Unaffected individuals have repeat numbers of up to 30, while individuals at a high risk of developing HD carry more than 37 CAG repeats. Individuals with 30-37 repeats have a high risk of passing on repeats in the affected size range to their offspring (Andrew et al., (1997) *Hum. Mol. Genet.*, 6:2005-2010; Duyao et al., (1993) *Nature Genet.*, 4:387-392; and Snell et al., (1993) *Nature Genet.*, 4:393-397).

It is known that patients are able to survive and live healthy lives with only one functioning copy of the IT15 gene. Thus, selective inactivation of the allele with a disease-causing mutation should diminish or even eliminate the disease while improving the possibilities of survival in heterozygous patients.

The combination of emotional, cognitive and motor symptoms in HD contributes to an unusually high cost of care. People with Huntington's Disease require care from health professionals of many stripes, including general practitioners, neurologists, social workers, home health aides, psychologists, physical therapists, and speech/language pathologists.

Currently, there are a few diagnostic approaches for nucleic acid sequence identification. U.S. Patent Application Publication No. 20040048301 describes allele-specific primer extension in the presence of labeled nucleotides for sequence identification, but does not include allele-specific primer extension for enrichment of one allele over the other for further analysis of the allele of interest as part of the kit. WO Patent Application No. 2003100101 describes isolation of one sequence in a mixture by hybridization markers and single-strand specific nucleases for use in single-molecule analysis. U.S. Patent Application Publication No. 20030039964 describes a method for isolation of one sequence in a mixture by hybridization to a fixed probe, but does not disclose the use of reverse transcription. U.S. Pat. No. 6,013,431 describes a method for analysis of bases adjacent to a hybridized, immobilized oligo, but does not disclose enrichment of one allele over the other. WO Patent Application No. 9820166 describes a method for specific selection of one allele over the other, followed by mass spectroscopic analysis of the selected molecule, but does not disclose the use of reverse transcription. None of these references disclose methods and diagnostic kits for linking polymorphic sequences to expanded repeat mutations for improved allele-specific diagnosis.

U.S. Patent Publication No. 20040241854 (Davidson) discloses allele-specific inhibition of specific single nucleotide polymorphism variants, and presents data showing that "expanded CAG repeats and adjacent sequences, while accessible to RNAi, may not be preferential targets for silencing" thus describing the problem that our invention addresses (determining what SNP variant at a remote molecular position is linked to the expanded CAG repeat in a particular patient), but does not teach the use of reverse transcription using an allele-specific primer to solve this problem, nor otherwise disclose a method for how to solve this problem. U.S. Patent Publication No. 20060270623 (McSwiggen) discloses multiple siRNA sequences, including those comprising SNP variants, but does not provide any working examples regarding allele-specific RNA interference using these disclosed siRNA sequences, nor disclose how to determine which allele-specific siRNA to administer to a particular Huntington's disease human patient in order to effectively treat that patient's disease by suppression of only the expanded Huntington allele in that patient.

Accordingly, there is need in the art for novel compounds, methods, and kits for allele-specific diagnostics and therapies.

SUMMARY OF THE INVENTION

Applicants have invented methods and kits for determining which variant allele of a single nucleotide polymorphism ("SNP") located at a distance from a disease-causing mutation co-segregates with the disease-causing mutation. In other words, the invention will allow for the determination of which SNP allele is located on the same mRNA transcript as the transcribed disease-causing mutation.

In one aspect, the invention provides a method for determining which single nucleotide polymorphism variant of an allele from a gene isolated from a heterozygous patient is on the same mRNA transcript as a disease-causing mutation at a remote region of the gene's mRNA comprising: a) an allele-specific reverse transcription reaction using an allele-specific primer which recognizes one single nucleotide polymorphism variant, and b) analysis of an allele-specific cDNA product from the allele-specific reverse transcription reaction at the remote region of the gene to determine the presence or absence of the mutation on the allele-specific cDNA product, wherein the allele-specific primer is shorter than about 20 nucleotides. In one embodiment, the 3' end of the allele-specific primer is positioned at the single nucleotide polymorphism nucleotide position.

In another aspect, the invention provides a method of treating a patient comprising determining which SNP variant is on the same mRNA transcript as a disease-causing mutation according to the method recited above, and applying an allele-specific therapy to the SNP variant, wherein the allele-specific therapy comprises an siRNA comprising a double-stranded portion, wherein the single nucleotide polymorphism site is located within seven nucleotides from an end of the double stranded portion. The allele-specific therapy of the present invention includes by way of example allele-specific RNA interference using siRNA or shRNA.

In yet another aspect, the invention provides a kit for determining which single nucleotide polymorphism variant of an allele of a heterozygous patient is on the same mRNA transcript as a disease-causing mutation located at a remote region of the gene's mRNA comprising a) an allele-specific primer which recognizes one single nucleotide polymorphism variant, and b) a set of instructions, wherein the allele-specific primer is shorter than about 20 nucleotides. In one embodiment, the 3' end of the allele-specific primer is positioned at the single nucleotide polymorphism nucleotide position.

BRIEF DESCRIPTION OF FIGURES

FIG. 3 is an illustration of primers and molecular beacons.

DETAILED DESCRIPTION OF THE INVENTION

Figure 1:
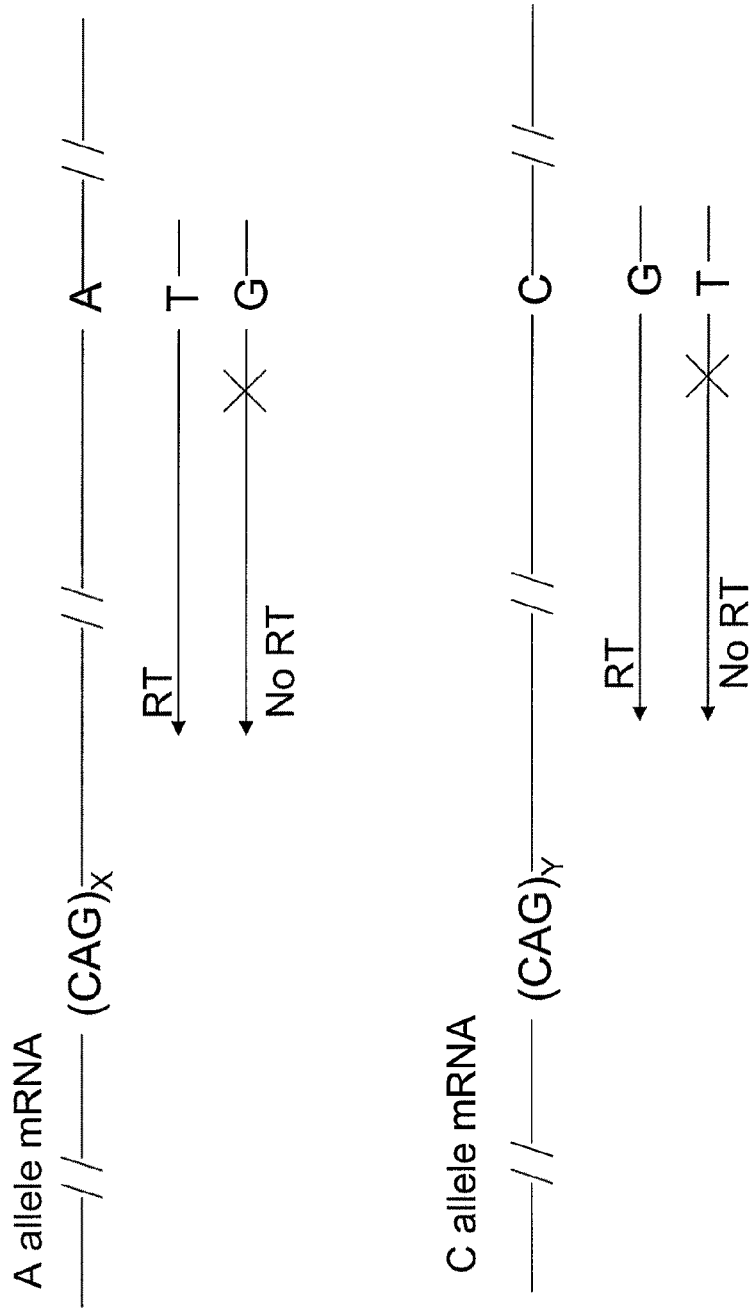
FIG. 1 is a schematic illustration of allele-specific reverse transcription for the "A" allele.

The present invention relates to methods and kits for performing allele-specific reverse transcription from an SNP site and analysis of a cDNA at a region of gene mutation. The methods, systems and reagents of the present invention are applicable to any disease which contains an SNP variant of an allele in a heterozygous subject that is on the same mRNA transcript as a disease-causing mutation that is at a remote region of the gene's mRNA.

To aid in the understanding of the invention, the following non-limiting definitions are provided:

The term "gene" refers to a DNA sequence that comprises control and coding sequences necessary for the production of a polypeptide or its precursor. The polypeptide can be encoded by a full length coding sequence (either genomic DNA or cDNA) or by any portion of the coding sequence so long as the desired activity is retained. In some aspects, the term "gene" also refers to an mRNA sequence or a portion thereof that directly codes for a polypeptide or its precursor.

The term "transfection" refers to the uptake of foreign DNA by a cell. A cell has been "transfected" when exogenous (i.e., foreign) DNA has been introduced inside the cell membrane. Transfection can be either transient (i.e., the introduced DNA remains extrachromosomal and is diluted out during cell division) or stable (i.e., the introduced DNA integrates into the cell genome or is maintained as a stable episomal element).

"Cotransfection" refers to the simultaneous or sequential transfection of two or more vectors into a given cell.

The term "promoter element" or "promoter" refers to a DNA regulatory region capable of being bound by an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences.

The term "in operable combination", "in operable order" or "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "vector" refers to a nucleic acid assembly capable of transferring gene sequences to target cells (e.g., viral vectors, non-viral vectors, particulate carriers, and liposomes). The term "expression vector" refers to a nucleic acid assembly containing a promoter which is capable of directing the expression of a sequence or gene of interest in a cell. Vectors typically contain nucleic acid sequences encoding selectable markers for selection of cells that have been transfected by the vector. Generally, "vector construct," "expression vector," and "gene transfer vector," refer to any nucleic acid construct capable of directing the expression of a gene of interest and which can transfer gene sequences to target cells. Thus, the term includes cloning and expression vehicles, as well as viral vectors.

The term "antibody" refers to a whole antibody, both polyclonal and monoclonal, or a fragment thereof, for example a F(ab)$_2$, Fab, FV, VH or VK fragment, a single chain antibody, a multimeric monospecific antibody or fragment thereof, or a bi- or multi-specific antibody or fragment thereof. The term also includes humanized and chimeric antibodies.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The term "patient" refers to a biological system to which a treatment can be administered. A biological system can include, for example, an individual cell, a set of cells (e.g., a cell culture), an organ, a tissue, or a multi-cellular organism. A patient can refer to a human patient or a non-human patient.

The terms "remote region" or "remote location" indicate a distance of at least 100 base pairs from the SNP site to the site of the disease-causing mutation, such as, for example, at least 0.5 kb, or at least 1 kb, or at least 2 kb or at least 3 kb, or at least 4 kb or at least 5 kb, or at least 6 kb or more.

The term "practitioner" refers to a person who uses methods, kits and compositions of the current invention on the patient. The term includes, without limitations, doctors, nurses, scientists, and other medical or scientific personnel.

The terms "siRNA molecule," "shRNA molecule," "RNA molecule," "DNA molecule," "cDNA molecule" and "nucleic acid molecule" are each intended to cover a single molecule, a plurality of molecules of a single species, and a plurality of molecules of different species.

The term "siRNA" refers to a double-stranded RNA molecule wherein each strand is between about 15 and about 30 bases of ribonucleic acid in length, and the two strands have a region of complementarity such that the two strands hybridize or "base pair" together through the annealing of complementary bases (Adenosine to Uracil, and Guanine to Cytosine). For some siRNA molecules, the two strands hybridize together in a manner such that there is an overhang of non-annealed bases at the 5' or 3' ends of the strand. For other siRNA molecules, the two strands hybridize together such that each base of one strand is paired with a base of the other strand. For some siRNA molecules, the two strands may not be 100% complementary, but may have some bases that do not hybridize due to a mismatch. For some siRNA molecules, the RNA bases may be chemically modified, or additional chemical moieties may be conjugated to one or more ends of one or more of the strands.

The term "shRNA" refers to a "short, hairpin" RNA molecule comprised of a single strand of RNA bases that self-hybridizes in a hairpin structure. The RNA molecule is comprised of a stem region of RNA bases that hybridize together to form a double-stranded region, and a loop region of RNA bases that form the bend of the hairpin. The term "shRNA" also refers to a DNA molecule from which a short, hairpin RNA molecule may be transcribed in vitro or in vivo.

The methods of the present invention utilize routine techniques in the field of molecular biology. Basic texts disclosing general molecular biology methods include Sambrook et al., *Molecular Cloning, A Laboratory Manual* (3d ed. 2001) and Ausubel et al., *Current Protocols in Molecular Biology* (1994).

The present invention relates generally to compositions and methods for diagnosing diseases which have an allele-specific therapy and a disease-causing mutation that is sufficiently distant from the molecular site of the therapy. Table 1 depicts certain diseases applicable to the present invention. Table 1 was derived from information previously published (DiProspero (2005)). Table 1 describes in part examples of triplet repeat expansion diseases and the mutant gene associated with each disease.

TABLE 1

Triplet Repeat Expansion Disorders
Noncoding repeats

| Disease | Symptoms | Gene | Locus | Protein |
| --- | --- | --- | --- | --- |
| Dystrophia myotonica 1 | Weakness, Myotonia | DMPK | 19q13 | Dystrophia myotonica Protein kinase |
| Spinocerebellar ataxia 8 | Ataxia | Antisense to KLHL1 | 13q21 | Undetermined |
| Huntington disease-like2 | Chorea, dementia | JPH3 | 16q24.3 | Junctophilin 3 |

Polyglutamine disorders

| Spinal and bulbar muscular atrophy | Weakness | AR | Xq13-q21 | Androgen receptor |
| --- | --- | --- | --- | --- |
| Huntington disease | Chorea, dementia | IT15 | 4P16.3 | Huntingtin |
| Dentatorubral-pallidoluysian atrophy | Ataxia, myoclonic epilepsy, dementia | DRPLA | 12p13.31 | Atrophin 1 |
| Spinocerebellar ataxia 1 | Ataxia | SCA1 | 6p23 | Ataxin 1 |
| Spinocerebellar ataxia 2 | Ataxia | SCA2 | 12q24.1 | Ataxin 2 |
| Spinocerebellar ataxia 3 (Machado-Joseph disease) | Ataxia | SCA3/MJD | 14q32.1 | Ataxin 3 |

TABLE 1-continued

Triplet Repeat Expansion Disorders
Noncoding repeats

| Disease | Symptoms | Gene | Locus | Protein |
|---|---|---|---|---|
| Spinocerebellar ataxia 6 | Ataxia | CACNA1A | 19p13 | $a_{1A}$-voltage-dependent calcium channel subunit |
| Spinocerebellar ataxia 7 | Ataxia | SCA7 | 3p12-p13 | Ataxin 7 |
| Spinocerebellar ataxia 17 | Ataxia | TBP | 6q27 | TATA box binding protein |
| Polyalanine disorders* | | | | |
| Oculopharyngeal dystrophy | Weakenss | PABPN1 | 14q11.2-q13 | Poly(A)-binding protein 2 |
| Congenital central hypoventilation syndrome | Respiratory difficulties | PHOX2B | 4p12 | Paired-like homeobox 2B |
| Infantile spasms | Mental retardation, epilepsy | ARX | Xp22.13 | Aristaless-related homeobox, X-linked |
| Synpolydactyly | Limb malformation | HOXD13 | 2q31-q32 | Homeobox D13 |

*Polyalanine expansions have also been reported among mutations in other genes, including RUNX2 (runt-related transcription factor2) in cleidocranial dysplasia, ZIC2 (Zic family member 2) in holoprosencephaly HOXA13 (homeobox A13) in hand-foot-genital syndrome, and FOXL2 (forkhead box L2) in type II blepharophimosis, ptosis, and epicanthus inversus syndrome. Small aspartic acid repeat expansions have been reported among other mutations in the COMP (cartilage oligomeric mat4rix protein) gene in patients with multiple epiphyseal dysplasia.

The present invention is not limited to the diseases described above. There may be situations where a disease is caused by many different mutations in a single gene (thus designing many different gene-targeting therapies may not be practical from a commercial perspective). However, if one or two expressed SNPs are present in the disease-associated gene, then the SNPs may actually serve as the molecular target for the therapy (and thus determination of linkage of the SNP to the disease-causing mutation would be essential).

For purposes of illustration, only HD will be discussed herein as an example of a triplet repeat expansion disease and example of the applicability of the present invention in providing methods and kits for determining allele-specific reverse transcription from an SNP site and analysis of a cDNA at a region of mutation.

The coding region of the IT15 gene is about 13,000 bases long. The HD disease-causing mutation is the expansion of the CAG repeat region. The CAG repeat region starts at about nucleotide position 15. If the CAG triplets repeat for about 25 or 30 times, the patient is not at risk of the disease. If however, more than 37 CAG repeats occur in a row on the nucleotide sequence then the patient is going to get Huntington's disease.

About ten thousand bases downstream from the CAG repeat sequence, there is a natural variation (Single Nucleotide Polymorphism, or SNP) of the IT15 gene in the human population, where for many people it might be an "A residue" and for many others it is a "C residue". That is just a normal variation, as it does not cause any disease. The information about the SNP can be used to determine that a child of a Huntington's disease patient has inherited an allele with the "A residue" from one parent and an allele with the "C residue" from the other parent.

The practitioner also knows that one of the patient's parents has HD and would like to know if the patient will also get HD. The practitioner can actually determine whether the patient is going to get HD or not, by looking at both of the patient's IT15 alleles, and determining how many CAG repeats the gene contains. If one of the CAG repeats is longer than 37, then the patient will get HD. Further, the practitioner can determine whether the patient is heterozygous (i.e., one allele has a normal number of repeats, e.g., 20, while the other allele has expanded repeats, e.g., 37). Analyzing the IT15 gene downstream of the CAG repeats, the practitioner may find that the patient received a "C residue" from one parent and an "A residue" from the other parent. Thus, the crucial issue for the allele-specific diagnosis is which SNP is on the same mRNA transcript as the expanded number of repeats in the patient's IT15 gene. Isolating the genetic information from the patient's parents may not help because it is possible that one or both parents are also heterozygous (e.g., each parent has two SNP variants of the gene (i.e., an A residue and a C residue variants). This disclosure provides a method of determining which SNP allele of the gene co-segregates with the disease-causing mutation.

One aspect of the present invention provides a diagnostic test, allowing the practitioner to determine which allele, classified by the nucleotide at the SNP position, co-segregates with the disease-causing mutation. In one embodiment, the test comprises a method for determining which single nucleotide polymorphism variant of an allele from a gene isolated from a heterozygous patient is on the same mRNA transcript as a disease-causing mutation at a remote region of the gene's mRNA comprising: a) an allele-specific reverse transcription reaction using an allele-specific primer which recognizes one single nucleotide polymorphism variant, wherein the 3' end of the allele-specific primer is positioned at the single nucleotide polymorphism nucleotide position, and b) analysis of an allele-specific cDNA product from the allele-specific reverse transcription reaction at the remote region of the gene to determine the presence or absence of the mutation on the allele-specific cDNA product. The inventors have discovered that the primer should preferably be shorter than about 20 nucleotides, e.g., about 15 nucleotides, long, because of a possibility that primers which are longer than about 20 nucleotides will not discriminate between the targeted SNP variants.

In a layman's terms, the practitioner takes RNA from the patient and applies a reverse transcription primer that recognizes just the "A allele." The "A allele" specific primer will have at its 3' position a complement to the SNP variant of interest. In case of the A-variant, the "A allele" specific primer will have the T at the 3' end, and so when this "A allele" specific primer anneals to the mRNA, it will base-pair with the 3' end and allow the reverse transcriptase to proceed to synthesize the cDNA from the "A allele." Conversely, the "A allele" primer will not base-pair at the 3' end of the primer with the "C allele" (since T is not complementary to C). Thus, the reverse transcription polymerase will not be able to produce cDNA from the C allele. On the other hand, in the "A" portion of a reaction, the practitioner will obtain a pool of the cDNAs that corresponds to the "A allele." The reaction can be repeated in a separate tube with a "C allele" specific primer and no "A allele" primer. A person of ordinary skill in the art will understand that the "C allele" specific primer will have a G on its 3' end. Essentially the practitioner will perform at least one allele-specific reverse transcription reaction, but preferably two allele-specific reverse transcriptions reactions (each with its own allele-specific primer), on the mRNA from the patient. As a result, the practitioner will have two subpopulations of cDNA, wherein each subpopulation is allele-specific, and the practitioner knows which pool corresponds to which variant. Thus, the practitioner will be able to use any number of possible methods, the simplest being PCR to analyze the upstream portion of the cDNA containing the CAG repeat region and quantify the number of the repeats from the cDNA products that came specifically from the "C reaction" or specifically from the "A reaction."

The embodiment of the invention described above employs the notion that a mismatch on the 3' position of the allele-specific primer will not allow reverse transcriptase to produce cDNA from the allele with a mismatched SNP variant. A person of ordinary skill in the art will undoubtedly recognize that the 3' end of the allele-specific primer does not have to be positioned at the single nucleotide polymorphism nucleotide position. For example, a skilled artisan may design primers and conditions of the reverse transcription reaction in such a way that the allele-specific primer will not bind altogether and thus lead to the same end result: absence of cDNA the allele with a mismatched SNP variant.

The accurate determination of the number of CAG repeats is required for the DNA-based predictive testing of at-risk individuals. To date, CAG repeat length determination is based on polymerase chain reaction (PCR) amplification of genomic DNA using primers flanking the CAG repeat region in the IT15 gene, and subsequent electrophoretic separation of the products in denaturing polyacrylamide gels (Williams et al., (1999) Comparative semi-automated analysis of (CAG) repeats in the HD gene: use of internal standards. *Mol. Cell. Probes*, 13:283-289).

Numerous methods and commercial kits for the synthesis of first strand cDNA molecules are well known in the art. Examples include the Superscript™ Double Strand cDNA Synthesis Kit (Invitrogen, Carlsbad, Calif.), the Array 50™, Array 350™ and Array 900™ Detection Kits (Genisphere, Hatfield, Pa.), and the CyScribe™ Post-Labelling Kit (Amersham, Piscataway, N.J.). RNA molecules (e.g., mRNA, hnRNA, rRNA, tRNA, miRNA, snoRNA, non-coding RNAs) from a source of interest are used as templates in a reverse transcription reaction. The RNA may be obtained from a mammalian or more preferably human tissue or cell source. The methods of the present invention are particularly suited for amplification of RNA from small numbers of cells, including single cells, which can be purified from complex cellular samples using, e.g., micromanipulation, fluorescence-activated cell sorting (FACS) and laser microdissection techniques (see Player et al., *Expert Rev. Mol. Diagn.* 4:831 (2004)).

Any reverse transcriptase can be used in the initial reverse transcription reaction, including thermostable, RNAse H$^+$ and RNase H$^-$ reverse transcriptases. Preferably, an RNase H$^-$ reverse trancriptase is used.

Primers for first strand cDNA synthesis can be obtained commercially or synthesized and purified using techniques well known in the art. As disclosed above, the inventors discovered that primers which are about 15 nucleotides long provide the best results in terms of discriminating between the SNP variants and efficiency in producing the allele-specific cDNA.

PCR amplifications of the CAG repeat region have primarily been performed by incorporating [a-$^{32}$P]dNTPs, or using $^{32}$P or fluorescently end-labeled primers. Sizing of fluorescently end-labeled amplification products was performed in various Applied Biosystems DNA sequencers (Andrew et al., (1993) *Nature Genet.*, 4:398-403; Choudhry et al., (2001) *Hum. Mol. Genet.*, 10:2437-2446; Ishii et al., (2001) *J. Clin. Endocrinol. Metab.*, 86:5372-5378; Le et al., (1997) *Mol. Pathol.*, 50:261-265; Mangiarini et al., (1997) *Nature Genet.*, 15:197-200; Pelotti et al., (2001) *Am. J. Forensic Med. Pathol.*, 22:55-57; Wallerand et al., (2001) *Fertil. Steril.*, 76:769-774; Warner et al., (1993) *Mol. Cell Probes*, 7:235-239; and Warner et al., (1996) *J. Med. Genet.*, 33:1022-1026).

High-resolution method can be used for the exact length determination of CAG repeats in HD genes as well as in genes affected in related CAG repeat disorders (Elisabeth Möncke-Buchner et al., Nucleic Acids Res. 2002 Aug. 15; 30(16)).

A wide variety of kits may be prepared according to present invention. For example, a kit may include a single stranded promoter template comprising at least one RNA polymerase recognition sequence; and instructional materials for synthesizing cDNA molecules using said promoter template. While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

The kits of the present invention may further include one or more of the following components or reagents: a reverse transcriptase (preferably with DNA-dependent DNA polymerase activity); an RNase inhibitor; an enzyme for attaching a 3' oligodeoxynucleotide tail onto DNA molecules (e.g., terminal deoxynucleotidyl transferase); an enzyme for degrading RNA in RNA/DNA duplexes (e.g., RNase H); and one or more RNA polymerases (e.g., T7, T3 or SP6 RNA polymerase). Additionally, the kits may include buffers, primers (e.g., oligodT primers, random primers), nucleotides, labeled nucleotides, an RNase inhibitor, polyA polymerase, RNase-free water, containers, vials, reaction tubes, and the like compatible with the synthesis of sRNA molecules according to the methods of the present invention. The components and reagents may be provided in containers with suitable storage media.

A person of ordinary skill in the art will appreciate that such allele-specific diagnosis empowers a practitioner to devise and implement an allele-specific treatment which generally comprises inactivation of the mutated copy of the gene. It is known that patients are able to survive and live healthy lives with only one functioning copy of the HD gene. It is known that the expression of the mutant gene is causing the trouble for the HD patient. Applicants' therapeutic model provides for selectively shutting off mutant gene expression without affecting expression of the normal gene, and is applicable to any disease which contains an SNP variant of an allele in a heterozygous subject that is on the same mRNA transcript as a disease-causing mutation that is at a remote region of the gene's mRNA.

Accordingly, another aspect of the present invention provides a method of treating a patient susceptible to Huntington's disease comprising: a) determining which single nucleotide polymorphism variant is on the same mRNA transcript as a disease-causing mutation according to an allele-specific reverse transcription reaction using an allele-specific primer which recognizes one single nucleotide polymorphism variant, wherein further the 3' end of the primer is positioned at the single nucleotide polymorphism nucleotide position, and b) analysis of the resulting cDNA product from the reverse transcription reaction at the region of the mutation to determine the presence or absence of the mutation on this allele-specific cDNA product, and c) applying an allele-specific therapy to the SNP variant. In one embodiment, the allele-specific therapy comprises an RNA molecule comprising a double-stranded portion, wherein the single nucleotide polymorphism site is located within seven nucleotides from an end of the double stranded portion. In one embodiment, the double stranded portion is between 15 and 23 nucleotides long, e.g., about 19 nucleotides long. Further, as discussed above, the siRNA molecule may contain a loop (e.g., shRNA), a 3' overhand or a 5' overhang which are outside of the double-stranded portion. The instant invention also provides a method of allele-specific therapy, wherein the double stranded portion does not contain a mismatch in a position adjacent to the single nucleotide polymorphism site. Thus, in one embodiment of the invention, the siRNA molecule does not contain any mismatches and one strand of the double-stranded portion is 100% identical to the portion of the targeted mRNA transcript. In one embodiment, wherein the disease treated by the allele-specific therapy is Huntington's disease, the non-limiting example of a single nucleotide polymorphism site suitable for the allele-specific therapy is rs262125.

It should be noted that the allele-specific therapy could itself operate at a different SNP site than the SNP site used to make the determination about which allele contains the mutation, so long as the SNP site of the therapy target and the SNP site used to identify the mutation-containing allele are already determined, before the therapy is administered to the patient, to be linked; that is, on the same mRNA transcript.

In some embodiments of the present invention the allele-specific therapy comprises allele-specific RNA interference using siRNA or shRNA. In this embodiment of the invention, the allele-specific therapy destroys the "A allele" of the patient. In this embodiment the siRNA targets the "A allele" upon introduction into the subject's brain by any method known to those of skill in the art (See for example, U.S. application Ser. No. 11/253,393, U.S. application Ser. No. 10/852,997, U.S. application Ser. No. 10/721,693, U.S. application Ser. No. 11/157,608, and PCT Patent Application No. US05/022156, which are incorporated herein in their entirety). When the siRNA is delivered into a cell it is used by proteins in the cell (known as the RISC complex) to find and destroy the mRNA from the Huntington's gene that has the "A allele." Thus, the messenger RNA is destroyed before it can be used to make protein. Conversely, the allele that came from the healthy parent does not get destroyed and so its messenger RNA still survives to be used to make functional biologically active protein.

The design and use of small interfering RNA complementary to mRNA targets that produce particular proteins is a recent tool employed by molecular biologists to prevent translation of specific mRNAs. Various groups have been recently studying the effectiveness of siRNAs as biologically active agents for suppressing the expression of specific proteins involved in neurological disorders. Caplen et al. *Human Molecular Genetics*, 11(2): 175-184 (2002) assessed a variety of different double stranded RNAs for their ability to inhibit cell expression of mRNA transcripts of the human androgen receptor gene containing different CAG repeats. Their work found gene-specific inhibition occurred with double stranded RNAs containing CAG repeats only when flanking sequences to the CAG repeats were present in the double stranded RNAs. They were also able to show that constructed double stranded RNAs were able to rescue caspase-3 activation induced by expression of a protein with an expanded polyglutamine region. Xia, Mao, et al., *Nature Biotechnology*, 20: 1006-1010 (2002) demonstrated the inhibition of polyglutamine (CAG) expression in engineered neural PC12 clonal cell lines that express a fused polyglutamine-fluorescent protein using constructed recombinant adenovirus expressing siRNAs targeting the mRNA encoding green fluorescent protein.

One aspect of the present invention provides an siRNA molecule corresponding to at least a portion of a gene containing an SNP variant of an allele in a heterozygous subject that is on the same mRNA transcript as a disease-causing mutation located at a remote region of the gene's mRNA, wherein such siRNA nucleic acid sequence is capable of inhibiting expression of the mRNA transcript containing the disease-causing mutation in a cell. siRNAs are typically short (19-29 nucleotides), double-stranded RNA molecules that cause sequence-specific degradation of complementary target mRNA known as RNA interference (RNAi). Bass, *Nature* 411:428 (2001).

Accordingly, in some embodiments, the siRNA molecules comprise a double-stranded structure comprising a sense strand and an antisense strand, wherein the antisense strand comprises a nucleotide sequence that is complementary to at least a portion of a desired nucleic acid sequence and the sense strand comprises a nucleotide sequence that is complementary to at least a portion of the nucleotide sequence of said antisense region, and wherein the sense strand and the antisense strand each comprise about 19-29 nucleotides.

Any desired nucleic acid sequence can be targeted by the siRNA molecules of the present invention. Nucleic acid sequences encoding desired gene targets are publicly available from Genbank.

The siRNA molecules targeted to desired sequence can be designed based on criteria well known in the art (e.g., Elbashir et al., *EMBO J*. 20:6877 (2001)). For example, the target segment of the target mRNA preferably should begin with AA (most preferred), TA, GA, or CA; the GC ratio of the siRNA molecule preferably should be 45-55%; the siRNA molecule preferably should not contain three of the same nucleotides in a row; the siRNA molecule preferably should not contain seven mixed G/Cs in a row; the siRNA molecule preferably should comprise two nucleotide overhangs (preferably TT) at each 3' terminus; the target segment preferably should be in the ORF region of the target mRNA and preferably should be at least 75 bp after the initiation ATG and at least 75 bp before the stop codon; and the target segment preferably should not contain more than 16-17 contiguous base pairs of homology to other coding sequences.

Based on some or all of these criteria, siRNA molecules targeted to desired sequences can be designed by one of skill in the art using the aforementioned criteria or other known criteria (e.g., Gilmore et al., *J. Drug Targeting* 12:315 (2004); Reynolds et al., *Nature Biotechnol.* 22:326 (2004); Ui-Tei et al., *Nucleic Acids Res.* 32:936 (2004)). Such criteria are available in various web-based program formats useful for designing and optimizing siRNA molecules (e.g., siDESIGN Center at Dharmacon; BLOCK-iT RNAi Designer at Invitrogen; siRNA Selector at Wistar Institute; siRNA Selection Program at Whitehead Institute; siRNA Design at Integrated DNA Technologies; siRNA Target Finder at Ambion; and siRNA Target Finder at Genscript).

siRNA molecules targeted to desired sequences can be produced in vitro by annealing two complementary single-stranded RNA molecules together (one of which matches at least a portion of a desired nucleic acid sequence) (e.g., U.S. Pat. No. 6,506,559) or through the use of a short hairpin RNA (shRNA) molecule which folds back on itself to produce the requisite double-stranded portion (Yu et al., *Proc. Natl. Acad. Sci. USA* 99:6047 (2002)). Such single-stranded RNA molecules can be chemically synthesized (e.g., Elbashir et al., *Nature* 411:494 (2001)) or produced by in vitro transcription using DNA templates (e.g., Yu et al., *Proc. Natl. Acad. Sci. USA* 99:6047 (2002)). When chemically synthesized, chemical modifications can be introduced into the siRNA molecules to improve biological stability. Such modifications include phosphorothioate linkages, fluorine-derivatized nucleotides, deoxynucleotide overhangs, 2'-β-methylation, 2'-O-allylation, and locked nucleic acid (LNA) substitutions (Dorset and Tuschl, *Nat. Rev. Drug Discov.* 3:318 (2004); Gilmore et al., *J. Drug Targeting* 12:315 (2004)).

siRNA molecules targeted to desired target sequences can be introduced into cells to inhibit expression. Alternatively, DNA molecules from which shRNA molecules targeted to desired target sequences can be introduced into cells to inhibit expression. Accordingly, another aspect of the present invention provides for inhibiting expression of an mRNA sequence containing an SNP allele and a disease-causing mutation in a cell comprising introducing into a cell at least one siRNA molecule or shRNA molecule that corresponds to at least a portion of the mRNA nucleic acid sequence. Any cell can be targeted. For example, the siRNA or shRNA molecules are introduced into a heart cell or brain cell. In some embodiments, the brain cell is from a subject at risk for HD, i.e., the offspring of a HD patient.

The siRNA molecules produced herein can be introduced into cells in vitro or ex vivo using techniques well-known in the art, including electroporation, calcium phosphate co-precipitation, microinjection, lipofection, polyfection, and conjugation to cell penetrating peptides (CPPs). The siRNA molecules can also be introduced into cells in vivo by direct delivery into specific organs such as the liver, brain, eye, lung and heart, or systemic delivery into the blood stream or nasal passage using naked siRNA molecules or siRNA molecules encapsulated in biodegradable polymer microspheres (Gilmore et al., *J. Drug Targeting* 12:315 (2004)).

Alternatively, siRNA molecules targeted to specific mRNA sequences can be introduced into cells in vivo by endogenous production from an expression vector(s) encoding the sense and antisense siRNA sequences. Accordingly, another aspect of the present invention provides an expression vector comprising at least one DNA sequence encoding a siRNA molecule corresponding to at least a portion of a specific mRNA nucleic acid sequence capable of inhibiting expression of a specific mRNA in a cell operably linked to a genetic control element capable of directing expression of the siRNA molecule in a cell. Expression vectors can be transfected into cells using any of the methods described above.

Genetic control elements include a transcriptional promoter, and may also include transcription enhancers to elevate the level of mRNA expression, a sequence that encodes a suitable ribosome binding site, and sequences that terminate transcription. Suitable eukaryotic promoters include constitutive RNA polymerase II promoters (e.g., cytomegalovirus (CMV) promoter, the SV40 early promoter region, the promoter contained in the 3' long terminal repeat of Rous sarcoma virus (RSV), the herpes thymidine kinase (TK) promoter, and the chicken beta-actin promoter), cardiac-tissue-specific RNA polymerase II promoters (e.g., the ventricular myosin light chain 2 (MLC-2v) promoter, and the sodium-calcium exchanger gene H1 promoter (NCX1H1)), and RNA polymerase III promoters (e.g., U6, H1, 7SK and 7SL).

In some embodiments, the sense and antisense strands of siRNA molecules are encoded by different expression vectors (i.e., cotransfected) (e.g., Yu et al., *Proc. Natl. Acad. Sci. USA* 99:6047 (2002). In other embodiments, the sense and antisense strands of siRNA molecules are encoded by the same expression vector. The sense and antisense strands can be expressed separately from a single expression vector, using either convergent or divergent transcription (e.g., Wang et al., *Proc. Natl. Acad. Sci. USA* 100:5103 (2003); Tran et al., *BMC Biotechnol.* 3:21 (2003)). Alternatively, the sense and antisense strands can be expressed together from a single expression vector in the form of a single hairpin RNA molecule, either as a short hairpin RNA (shRNA) molecule (e.g., Arts et al., *Genome Res.* 13:2325 (2003)) or a long hairpin RNA molecule (e.g., Paddison et al., *Proc. Natl. Acad. Sci. USA* 99:1443 (2002)).

Although numerous expression vectors can be used to express siRNA molecules in cells (Dorsett and Tuschl, *Nat. Rev. Drug Discov.* 3:318 (2004)), viral expression vectors are preferred, particularly those that efficiently transduce heart cells (e.g., alphaviral, lentiviral, retroviral, adenoviral, adeno-associated viral (AAV)) (Williams and Koch, *Annu. Rev. Physiol.* 66:49 (2004); del Monte and Hajjar, *J. Physiol.* 546.1:49 (2003). Both adenoviral and AAV vectors have been shown to be effective at delivering transgenes (including transgenes directed to diseases) into heart, including failing cardiomyocytes (e.g., Iwanaga et al., *J. Clin. Invest.* 113:727 (2004); Seth et al., *Proc. Natl. Acad. Sci. USA* 101:16683 (2004); Champion et al., *Circulation* 108:2790 (2003); Li et al., *Gene Ther.* 10:1807 (2003); Vassalli et al., *Int. J. Cardiol.* 90:229 (2003); del Monte et al., *Circulation* 105:904 (2002); Hoshijima et al., *Nat. Med.* 8:864 (2002); Eizema et al., *Circulation* 101:2193 (2000); Miyamoto et al., *Proc. Natl. Acad. Sci. USA* 97:793 (2000); He et al., *Circulation* 100:974 (1999). Recent reports have demonstrated the use of AAV vectors for sustained gene expression in mouse and hamster myocardium and arteries for over one year (Li et al., *Gene Ther.* 10:1807 (2003); Vassalli et al., *Int. J. Cardiol.* 90:229 (2003)). In particular, expression vectors based on AAV serotype 6 have been shown to efficiently transduce both skeletal and cardiac muscle (e.g., Blankinship et al., *Mol. Ther.* 10:671 (2004)). The present invention also provides for the use of coxsackie viral vectors for delivery of desired siRNA sequences.

Following introduction of the desired siRNA molecules into cells, changes in desired gene product levels can be measured if desired. Desired gene products include, for example, desired mRNA and desired polypeptide, and both can be measured using methods well-known to those skilled in the art. For example, desired mRNA can be directly detected and quantified using, e.g., Northern hybridization, in situ hybridization, dot and slot blots, or oligonucleotide arrays, or can be amplified before detection and quantitation using, e.g., polymerase chain reaction (PCR), reverse-transcription-PCR (RT-PCR), PCR-enzyme-linked immunosorbent assay (PCR-ELISA), or ligase chain reaction (LCR).

Desired polypeptide (or fragments thereof) can be detected and quantified using various well-known immunological assays, such as, e.g., enzyme-linked immunosorbent assay (ELISA), radioimmunoassay (RIA), immunoprecipitation, immunofluorescence, and Western blotting. Anti-desired antibodies (preferably anti-human desired) for use in immunological assays are commercially available from, e.g., EMD Biosciences (San Diego, Calif.), Upstate (Charlottesville, Va.), Abcam (Cambridge, Mass.), Affinity Bioreagents (Golden, Colo.) and Novus Biologicals (Littleton, Colo.), or may be produced by methods well-known to those skilled in the art.

Specific embodiments according to the methods of the present invention will now be described in the following examples. The examples are illustrative only, and are not intended to limit the remainder of the disclosure in any way.

EXAMPLES

Example 1

RNA-Isolation and Reverse Transcription Reaction

Applicants analyzed the CAG-repeat sequences in the Huntington's disease gene using the following allele-specific reverse transcription reaction. Table 2 defines the sequences for various allele-specific reverse transcription primers for use in determining which allele of a heterozygous patient's Huntington's disease gene contains the disease-causing allele, in accordance with the subject invention. The subject SNP sites in the Huntington's disease gene (IT15) are designated using the identification number provided by the National Center for Biotechnology Information (NCBI) database, accessible at: http://www.ncbi.nlm.nih.gov/entrez/query.fcgi?db=snp.

TABLE 2

SNP NCBI: rs1936032

| | Allele C | | | Allele G | |
|---|---|---|---|---|---|
| SEQ. ID. | Name | Sequence | SEQ. ID. | Name | Sequence |
| 1 | 1936032C9 | AAGCCTAAG | 11 | 1936032G9 | AAGCCTAAC |
| 2 | 1936032C10 | TAAGCCTAAG | 12 | 1936032G10 | TAAGCCTAAC |
| 3 | 1936032C11 | GTAAGCCTAAG | 13 | 1936032G11 | GTAAGCCTAAC |
| 4 | 1936032C12 | AGTAAGCCTAAG | 14 | 1936032G12 | AGTAAGCCTAAC |
| 5 | 1936032C13 | GAGTAAGCCTAAG | 15 | 1936032G13 | GAGTAAGCCTAAC |
| 6 | 1936032C14 | CGAGTAAGCCTAAG | 16 | 1936032G14 | CGAGTAAGCCTAAC |
| 7 | 1936032C15 | ACGAGTAAGCCTAAG | 17 | 1936032G15 | ACGAGTAAGCCTAAC |
| 8 | 1936032C16 | AACGAGTAAGCCTAAG | 18 | 1936032G16 | AACGAGTAAGCCTAAC |
| 9 | 1936032C17 | GAACGAGTAAGCCTAAG | 19 | 1936032G17 | GAACGAGTAAGCCTAAC |
| 10 | 1936032C18 | GGAACGAGTAAGCCTAAG | 20 | 1936032G18 | GGAACGAGTAAGCCTAAC |

SNP NCBI: rs2530588

| | Allele C | | | Allele T | |
|---|---|---|---|---|---|
| SEQ. ID. | Name | Sequence | SEQ. ID. | Name | Sequence |
| 21 | 2530588C9 | GCTGAGCGG | 31 | 2530588T9 | GCTGAGCGA |
| 22 | 2530588C10 | GGCTGAGCGG | 32 | 2530588T10 | GGCTGAGCGA |
| 23 | 2530588C11 | AGGCTGAGCGG | 33 | 2530588T11 | AGGCTGAGCGA |
| 24 | 2530588C12 | AAGGCTGAGCGG | 34 | 2530588T12 | AAGGCTGAGCGA |
| 25 | 2530588C13 | CAAGGCTGAGCGG | 35 | 2530588T13 | CAAGGCTGAGCGA |
| 26 | 2530588C14 | CCAAGGCTGAGCGG | 36 | 2530588T14 | CCAAGGCTGAGCGA |
| 27 | 2530588C15 | TCCAAGGCTGAGCGG | 37 | 2530588T15 | TCCAAGGCTGAGCGA |
| 28 | 2530588C16 | ATCCAAGGCTGAGCGG | 38 | 2530588T16 | ATCCAAGGCTGAGCGA |
| 29 | 2530588C17 | CATCCAAGGCTGAGCGG | 39 | 2530588T17 | CATCCAAGGCTGAGCGA |
| 30 | 2530588C18 | ACATCCAAGGCTGAGCGG | 40 | 2530588T18 | ACATCCAAGGCTGAGCGA |

SNP NCBI: rs363125

| | Allele A | | | Allele C | |
|---|---|---|---|---|---|
| SEQ. ID. | Name | Sequence | SEQ. ID. | Name | Sequence |
| 41 | 363125A9 | GCGTTGAAT | 53 | 363125C9 | GCGTTGAAG |
| 42 | 363125A10 | AGCGTTGAAT | 54 | 363125C10 | AGCGTTGAAG |
| 43 | 363125A11 | TAGCGTTGAAT | 55 | 363125C11 | TAGCGTTGAAG |
| 44 | 363125A12 | CTAGCGTTGAAT | 56 | 363125C12 | CTAGCGTTGAAG |
| 45 | 363125A13 | TCTAGCGTTGAAT | 57 | 363125C13 | TCTAGCGTTGAAG |
| 46 | 363125A14 | TTCTAGCGTTGAAT | 58 | 363125C14 | TTCTAGCGTTGAAG |

TABLE 2-continued

| | | | | | | |
|---|---|---|---|---|---|---|
| 47 | 363125A15 | CTTCTAGCGTTGAAT | 59 | 363125C15 | CTTCTAGCGTTGAAG |
| 48 | 363125A16 | TCTTCTAGCGTTGAAT | 60 | 363125C16 | TCTTCTAGCGTTGAAG |
| 49 | 363125A17 | TTCTTCTAGCGTTGAAT | 61 | 363125C17 | TTCTTCTAGCGTTGAAG |
| 50 | 363125A18 | GTTCTTCTAGCGTTGAAT | 62 | 363125C18 | GTTCTTCTAGCGTTGAAG |
| 51 | 363125A19 | TGTTCTTCTAGCGTTGAAT | 63 | 363125C19 | TGTTCTTCTAGCGTTGAAG |
| 52 | 363125A20 | GTGTTCTTCTAGCGTTGAAT | 64 | 363125C20 | GTGTTCTTCTAGCGTTGAAG |

SNP NCBI: rs362331

| Allele C | | | Allele T | | |
|---|---|---|---|---|---|
| SEQ. ID. | Name | Sequence | SEQ. ID. | Name | Sequence |
| 65 | 362331C9 | CACACAGTG | 75 | 362331T9 | CACACAGTA |
| 66 | 362331C10 | GCACACAGTG | 76 | 362331T10 | GCACACAGTA |
| 67 | 362331C11 | TGCACACAGTG | 77 | 362331T11 | TGCACACAGTA |
| 68 | 362331C12 | GTGCACACAGTG | 78 | 362331T12 | GTGCACACAGTA |
| 69 | 362331C13 | AGTGCACACAGTG | 79 | 362331T13 | AGTGCACACAGTA |
| 70 | 362331C14 | AAGTGCACACAGTG | 80 | 362331T14 | AAGTGCACACAGTA |
| 71 | 362331C15 | GAAGTGCACACAGTG | 81 | 362331T15 | GAAGTGCACACAGTA |
| 72 | 362331C16 | TGAAGTGCACACAGTG | 82 | 362331T16 | TGAAGTGCACACAGTA |
| 73 | 362331C17 | ATGAAGTGCACACAGTG | 83 | 362331T17 | ATGAAGTGCACACAGTA |
| 74 | 362331C18 | GATGAAGTGCACACAGTG | 84 | 362331T18 | GATGAAGTGCACACAGTA |

Cell Culture and Genotyping.

Fibroblasts purchased from Coriell Cell Repositories (Camden, N.J.) were cultured at 37° C. with 5% $CO_2$ and maximum humidity. The growth medium was minimum essential medium containing 20% FBS, 1% PSN antibiotics, 1% fungizone, 2% non-essential amino acids, 2% amino acids and 2% vitamins (all reagents from Invitrogen). Genomic DNA was isolated using the DNeasy kit (Qiagen) and nucleotide identity for HD alleles at various SNP positions was determined by pyrosequencing conducted by Isogen Lifescience (The Netherlands).

Identification of a Heterozygous HD Individual.

Fibroblasts from 21 individuals from different kindreds, diagnosed with HD or known to be at risk for HD, were purchased from Coriell Cell Repositories (Camden, N.J.). DNA was harvested from each fibroblast culture and pyrosequenced to determine the nucleotide identity at eleven known single nucleotide polymorphism (SNP) sites within the protein coding region of the HD sequence. Heterozygosity was found at four of the eleven SNP sites tested. Ten of the 21 genotyped fibroblast cultures (see Table 3) were heterozygous for at least 1 SNP site. The results showed that the donor of GM04022 fibroblasts is heterozygous at SNP position rs363125 (NCBI), harboring both an A-allele (adenine) and a C-allele (cytosine) at nucleotide position 5310 in the HD reference sequence NM_002111.6. The fibroblasts from this donor (here called donor-1) were selected for further study. These fibroblasts are from a female Caucasian donor who was 28 years old at the time of cell collection. Her mother, who was 58 years old at the time of the cell collection, was reportedly diagnosed with HD at age 49.

TABLE 3

Genotype of DNA (coding strand) from fibroblast cells from Huntington's disease kindreds at SNP sites

| | SNP site: | | | | | |
|---|---|---|---|---|---|---|
| Cell line: | Rs1936033 | Rs1936032 | Rs2530588 | Rs4690074 | Rs3025837 | Rs363129 |
| GM00305 | T/T | G/G | C/C | C/C | A/A | C/C |
| GM01061 | T/T | G/G | C/C | T/C | A/A | C/C |
| GM01085 | T/T | G/G | C/C | C/C | A/A | C/C |
| GM01168 | T/T | G/G | C/C | C/C | A/A | C/C |
| GM01169 | T/T | G/G | C/C | T/C | A/A | C/C |
| GM01171 | T/T | G/G | C/C | C/C | A/A | C/C |
| GM01187 | T/T | G/G | C/C | C/C | A/A | C/C |
| GM02079 | T/T | G/G | C/C | C/C | A/A | C/C |
| GM02147 | T/T | G/G | C/C | T/C | A/A | C/C |
| GM02155 | T/T | C/G | C/C | C/C | A/A | C/C |
| GM02165 | T/T | G/G | C/C | C/C | A/A | C/C |
| GM02173 | T/T | G/G | C/C | T/C | A/A | C/C |

TABLE 3-continued

Genotype of DNA (coding strand) from fibroblast cells from Huntington's disease kindreds at SNP sites

| | | | | | | |
|---|---|---|---|---|---|---|
| GM02191 | T/T | G/G | C/C | T/C | A/A | C/C |
| GM03793 | T/T | G/G | C/C | C/C | A/A | C/C |
| GM03864 | T/T | G/G | C/C | C/C | A/A | C/C |
| GM04022 | T/T | C/G | C/C | C/C | A/A | C/C |
| GM04196 | T/T | G/G | C/C | T/C | A/A | C/C |
| GM04281 | T/T | G/G | C/C | C/C | A/A | C/C |
| GM04285 | T/T | G/G | C/C | C/C | A/A | C/C |
| GM04691 | T/T | G/G | C/C | C/C | A/A | C/C |
| GM09197 | T/T | G/G | C/C | T/C | A/A | C/C |
| % heterozygotes | 0% | 10% | 0% | 33% | 0% | 0% |

| Cell line: | SNP site: | | | | |
|---|---|---|---|---|---|
| | Rs363125 | Rs362331 | Rs362321 | Rs3025816 | Rs362308 |
| GM00305 | C/C | T/T | C/C | C/C | T/T |
| GM01061 | C/C | T/C | C/C | C/C | T/T |
| GM01085 | C/C | T/T | C/C | C/C | T/T |
| GM01168 | C/C | T/T | C/C | C/C | T/T |
| GM01169 | C/C | T/C | C/C | C/C | T/T |
| GM01171 | C/A | T/C | C/C | C/C | T/T |
| GM01187 | C/C | T/T | C/C | C/C | T/T |
| GM02079 | C/C | T/T | C/C | C/C | T/T |
| GM02147 | C/C | T/C | C/C | C/C | T/T |
| GM02155 | C/A | T/C | C/C | C/C | T/T |
| GM02165 | C/C | T/T | C/C | C/C | T/T |
| GM02173 | C/C | T/C | C/C | C/C | T/T |
| GM02191 | C/C | T/C | C/C | C/C | T/T |
| GM03793 | C/C | T/T | C/C | C/C | T/T |
| GM03864 | C/C | T/T | C/C | C/C | T/T |
| GM04022 | C/A | T/C | C/C | C/C | T/T |
| GM04196 | C/C | T/C | C/C | C/C | T/T |
| GM04281 | C/C | T/T | C/C | C/C | T/T |
| GM04285 | C/C | T/T | C/C | C/C | T/T |
| GM04691 | C/C | T/T | C/C | C/C | T/T |
| GM09197 | C/C | T/C | C/C | C/C | T/T |
| % heterozygotes | 14% | 48% | 0% | 0% | 0% |

Development of Allele-Specific Reverse Transcription.

As described above, donor-1 was determined to be heterozygous (adenine versus cytosine) at SNP site rs363125. In order to design an allele-specific RNA interference-based therapy for donor-1, it needs to be determined which of these SNP sequences is associated with the expanded CAG repeat mutation that is located approximately 5000 nucleotides upstream from the SNP position. Appropriate siRNA or shRNA targeting SNP site rs363125 should only reduce protein expression from the allele that contains the expanded CAG repeat and should therefore only be specific for the associated SNP. Correspondence between the SNP identity and the expanded allele cannot be readily determined by cDNA sequencing or by comparing the lengths of PCR products spanning the SNP position and the CAG repeat region. To solve this problem, the inventors developed a strategy that uses SNP-specific reverse transcription (RT) primers to selectively generate cDNA from only one allelic species of HD mRNA. The primers each contained either guanine or thymine at the 3' terminal position, corresponding to SNP site rs363125, as shown in FIG. 1. Primers of various lengths were tested. The 3'-guanine and 3'-thymine primer were each designed to specifically facilitate reverse transcription (also known as first strand synthesis) of only the mRNA containing cytosine or adenine at the SNP position, respectively. Following reverse transcription with either type of RT primer, PCR was conducted on the resulting cDNA using PCR primers that amplify a product spanning the CAG-repeat sequence in the first exon of the HD gene.

RNA isolated from the fibroblasts was reverse transcribed using the Superscript III RT kit (Invitrogen) in the presence of 100 nM of one of the following DNA primers: the 20-mer 5'-GTGTTCTTCTAGCGTTGAA<u>T</u>-3', SEQ ID NO: 52 (or a shorter, corresponding 15-mer or 10-mer ending in <u>T</u>-3', corresponding to SEQ ID NO: 47 and SEQ ID NO: 42, respectively) or the 20-mer primer 5'-GTGTTCTTCTAGCGT-TGAA<u>G</u>-3' SEQ ID NO: 64 (or a shorter, corresponding 15-mer or 10-mer primer ending in <u>G</u>-3', corresponding to SEQ ID NO: 59 and SEQ ID NO: 54, respectively) at 100 nM. The CAG repeat sequence on either RT product was then amplified by PCR (Bio-Rad iCycler) using Accuprime GC-Rich DNA-polymerase (Invitrogen), and forward primer 5'-GCCTTCGAGTCCCTCAAGT-3' and reverse primer 5'-GACAATGATTCACACGGTCT-3' at 0.2 µM each (SEQ ID NO: 85 and SEQ ID NO: 86, respectively). The resulting PCR products contain the complete CAG repeat sequence of one of the two alleles of the GM04022 cells. CAG-repeat size for each allelic RT products was determined using standard 1.5% agarose gel electrophoresis with ethidium bromide staining, and also by sequencing of the products of the PCR amplification of the CAG repeat region.

Gel electrophoresis of the respective PCR products (FIG. 2) showed that the RT-PCR assay using the 3'-thymine primer in the RT step yielded a product of approximately 300 base pairs. In contrast, the RT-PCR assay using the 3'-guanine primer in the RT step yielded a PCR product of approximately 360 base pairs. RT primers that were 15 bases in length yielded cDNA from which a PCR product corresponding to only one allele from heterozygous donor-1 was preferentially amplified. Allele specific RT primers of different lengths were also designed and tested for SNP1936032 and SNP362331, both of which were also determined to be heterozygous in donor-1 (Table 3). These experiments showed that primers of 15 bases in length were also optimal for allele-specific transcription from the respective SNP sites.

Correspondence Between a SNP Identity and an Individual's Expanded Allele.

Figure 2:
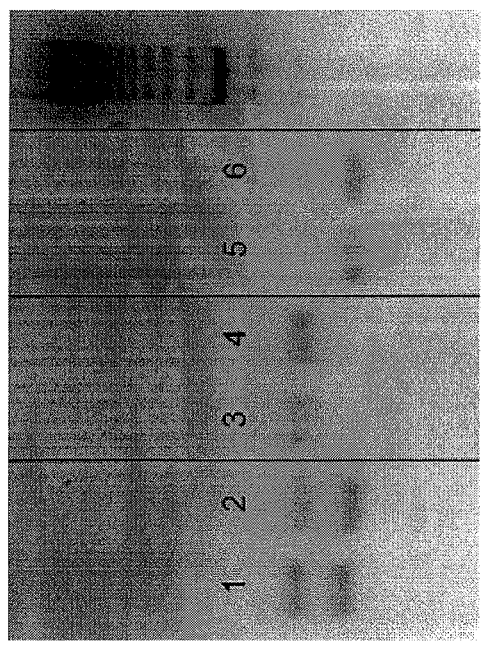
FIG. 2 is a photograph of a gel showing results of allele-specific reverse transcription.

Based on the relative sizes of the PCR products in FIG. 2, it may be determined that the CAG-repeat region on the allele containing cytosine at SNP rs363125 contains approximately 20 more repeats than the allele containing adenine at that SNP, with a total CAG-repeat length of about 40 repeats. Sequencing of the PCR products confirmed that the CAG repeat region of the donor-1 allele containing cytosine at SNP position rs363125 contains 44 versus 19 CAG codons, respectively. Therefore, the allele containing cytosine at SNP position rs363125 is the disease-causing allele, and an appropriate allele-specific therapy for donor-1 would deliver an siRNA or shRNA providing the sequence specified here as siRNA 363125_C-16.

Example 2

Development of SNP-Specific Real Time PCR Assays

In order to determine whether allele-specific suppression of HD mRNA is occurring in cells, it is necessary to be able to quantify the amount of HD mRNA corresponding to each allele individually. Molecular beacons are synthetic oligonucleotide probes that have a fluorophore and a quencher covalently linked to the respective ends of the oligo. In solution, the beacon adopts a hairpin conformation, causing the fluorophore to be quenched. However, upon hybridization with complementary DNA in a PCR reaction, the hairpin conformation is lost and fluorescence from the fluorophore can be detected. Beacons can be constructed such that as little as a single nucleotide mismatch between the beacon and the complementary DNA is sufficient for the probe to be more stable in its self-annealed state than in the probe-cDNA hybrid. The inventors designed two such beacons corresponding to the two allelic variants of SNP rs363125 (FIG. 3). Absence of genomic DNA carry over in the RNA isolates was confirmed by PCR using forward primer 5'-CTCGCCTC-CAGCATGAAAGT-3' and reverse primer 5'-GT-GACTGGGGCATTGATT-3', (SEQ ID NOs: 87 and 88, respectively) which amplify monocyte chemo-attractant protein-1 (MCP-1) genomic DNA. Genomic DNA from HeLa cells served as a positive control for the PCR reaction, and only total RNA samples from fibroblasts verified to be without detectable genomic DNA were used in further analyses. Concentration and integrity of the isolated RNA were checked by Experion automated electrophoresis (Bio-Rad, StdSens analysis kit) of the 28S/18S ribosomal RNA. RNA was reverse transcribed into cDNA using the iScript cDNA synthesis kit (BioRad), after which allele-specific real time PCR was conducted using the molecular beacon method. The sequences of the molecular beacons are described in FIG. 3 and correspond to SEQ ID NOs: 89 (3'-BHQI-tcacgca-GATCGCAACTT<u>A</u>ATGACAGGGtgcgtga-FAM-5') and 90 (3'-BHQI-gcgctagAGATCGCAACTT C<u>A</u>TGACAGGGGTAGctagcgc-FAM-5'), for the "A" and the "C" alleles, respectively. In these sequences, the "loop sequence" which binds to a portion of the targeted portion of the PCR product is in capital letters, while the "stem" portions, which form the double strand of the beacon if the beacon is not bound to the targeted portion of the PCR product. The sequences of the primers for the "A" allele correspond to SEQ ID NOs: 91 (5'-CCTTCTCTCCGTATT-TAATCTCCTGTA-3') and 92 (5'-TCATTTCCACCTTCAGCTGTTTTGTAA-3') for the forward and the reverse primers, respectively. The sequences of the primers for the "C" allele correspond to SEQ ID NOs 93 (5'-AGATATTGTTCTTTCTCGTATTCAGG-3') and 94

(5'-TGCTCACTCATTTCCACCTTC-3') for the forward and the reverse primers, respectively. Detection of the PCR product was conducted using molecular beacons (Proligo, France) each of which detects only a PCR product containing a complementary nucleotide at the SNP position. The two alleles were quantified in separate PCR reactions, each containing 0.3 µM of the appropriate molecular beacon. During elongation, increase of the FAM fluorescence signal was recorded. The data were quantified against a standard curve generated using a serial dilution of a plasmid containing the PCR product (Baseclear genesynthesis, The Netherlands). Results were normalized against GAPDH, amplified using IQ SYBR Green Supermix (Bio-Rad) with forward primer 5'-ACTCCTCCACCTTTGACGC-3' (SEQ ID NO: 95) and reverse primer 5'-GTTGCTGTAGCCAA-ATTCGTT-3' (SEQ ID NO: 96).

Figure 4:
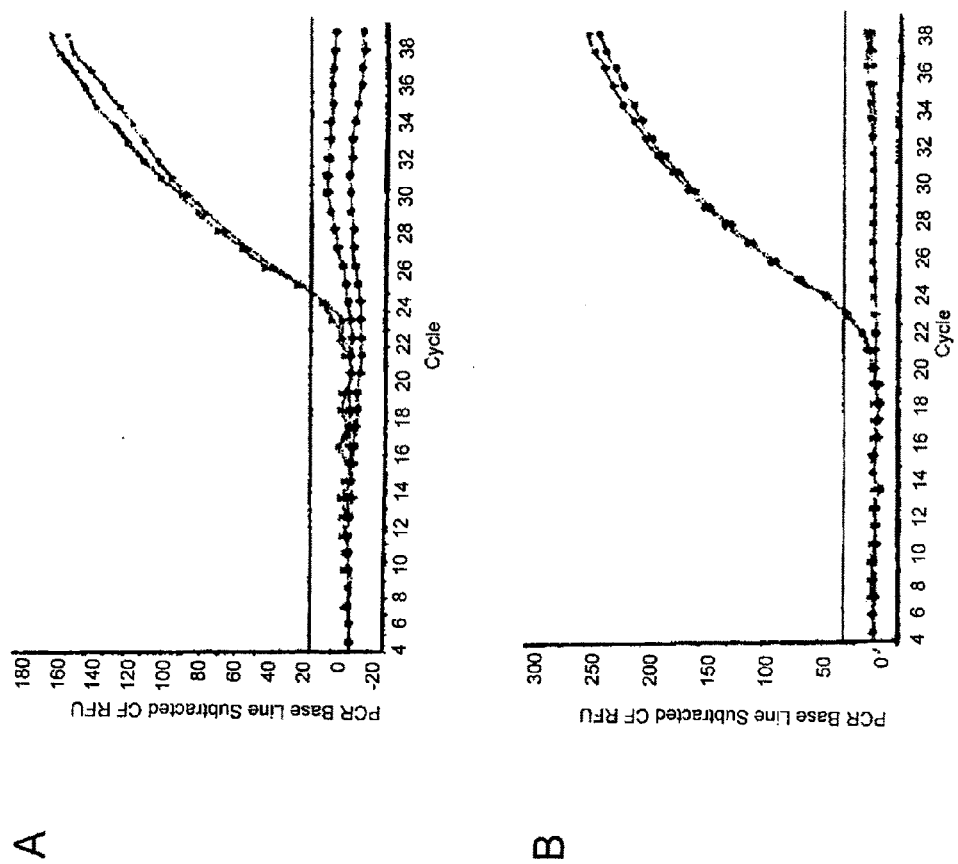
FIG. 4 is an illustration of allele specificity of the molecular beacons used for the allele-specific quantification of real-time PCR product

As shown in FIG. 4, these two beacons are specific for their respective SNP sequences in real time PCR reactions. In these PCR reactions plasmids were used as template DNA that were engineered and verified to contain one or the other allelic variant of the target sequence. Both beacon MB363125_A and MB363125_C were found to yield a PCR amplification signal only from their corresponding DNA template.

Allele-Specific Suppression of Huntingtin mRNA.

Fibroblasts were cultured in 25 $cm^2$ culture flasks (Nunc) as described, but without the addition of PSN antibiotics and Fungizone. Lipofectamine 2000 (Invitrogen) was used to conduct siRNA transfection at three different conditions: 1) mock transfection (n=8); 2) transfection with scrambled siRNA (Ambion) (n=4); and 3) transfection with siRNA sequence 5'-GAAGUACUGUCCCCAUCUCdTdT-3', SEQ ID NO: 97, (Ambion) (n=7) at a concentration of 100 nM. The latter siRNA has a guanine located at position 16 relative to the 3' end of the complementary region of the target huntingtin mRNA, providing specificity for the allele containing cytosine at the SNP position. A parallel cell culture was transfected with a fluorescently labeled Block-It siRNA (Invitrogen) to verify efficiency of Lipofectamine 2000 transfection. The cells were incubated overnight at 37° C., 5% $CO_2$ and maximum humidity. The cultures were then washed with PBS and fluorescence microscopy (Leica DM-IRB) was used to confirm transfection in the Block-It transfected cultures, which were considered representative for all transfection conditions. The cells were cultured for another day before RNA isolation as described, approximately 48 hours post-transfection.

Figure 5:
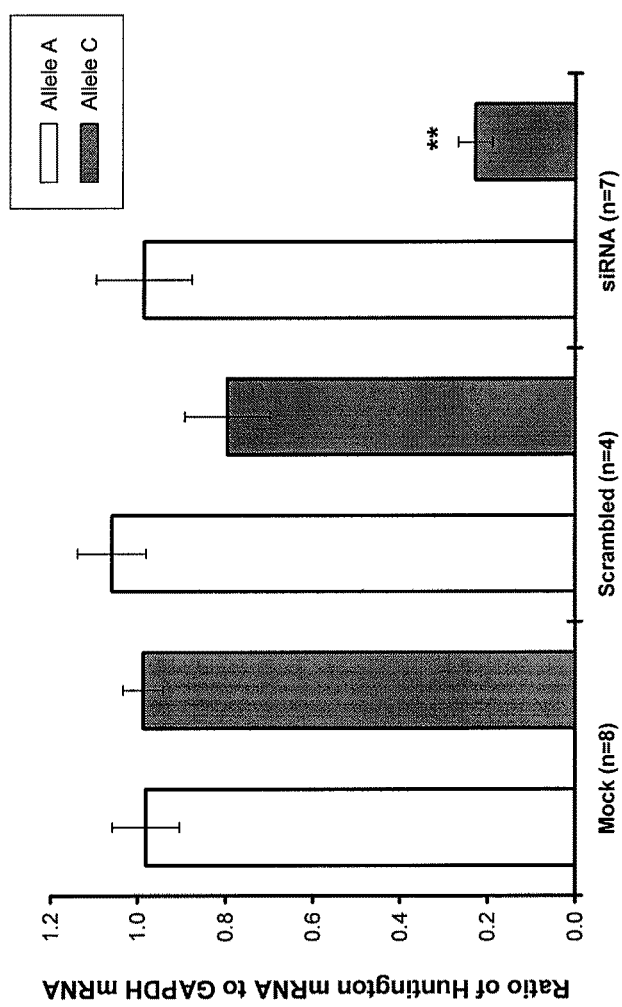
FIG. 5 illustrates that a siRNA molecule designated as 363125_C-16 inhibits the mutant, but not the wild-type huntingtin mRNA.

Fibroblasts from donor-1 were transfected with siRNA designed to specifically target the mRNA containing cytosine at SNP site rs363125. This siRNA molecule (siRNA 363125_C-16) was designed such that the cytosine nucleotide of the SNP is located at position 16 relative to the 5' end of the sense strand of the siRNA molecule. The amount of mRNA from both endogenous alleles was separately quantified using the molecular beacons developed to be specific for the allelic variants at this SNP site. The results showed that about 48 hours following treatment of the fibroblasts with siRNA 363125_C-16, mRNA transcripts containing cytosine at position rs363125 were detected at levels approximately 80% lower (p<0.01, two-tailed) from that detected in controls that were mock transfected, or transfected with a scrambled siRNA (FIG. 5; ANOVA of treatment by allele interaction effect, p=0.0002). Transcripts containing adenine at position rs363125 were present at levels statistically not different from (p=0.5145) and numerically similar to the controls.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

What is claimed:

1. A method for determining which single nucleotide polymorphism variant of an allele from a gene isolated from a heterozygous patient is on the same mRNA transcript as a disease-causing mutation at a remote region of the gene's mRNA comprising:

a) providing first allele-specific primer which recognizes a single nucleotide polymorphism (SNP) variant of a SNP in the mRNA transcript of said heterozygous patient, b) providing a second allele-specific primer which recognizes another variant of said SNP in the mRNA transcript of said heterozygous patient, c) conducting a reverse transcription reaction from said gene's mRNA using either the allele-specific primer of part (a) or the allele-specific primer of part (b);
d) providing a set of PCR primers flanking said disease-causing mutation and capable of hybridizing to the allele-specific cDNA product, and
e) amplifying said remote region of the allele-specific cDNA product using a said set of PCR primers,
wherein the allele-specific primer and the second allele-specific primer is shorter than 18 nucleotides.

2. The method of claim 1, wherein the 3' end of the allele-specific primer is positioned at the single nucleotide polymorphism nucleotide position.

3. The method of claim 1 wherein the 3' end of at least the second allele-specific primer is positioned at the single nucleotide polymorphism nucleotide position.

4. The method of claim 1 wherein the 3' end of at least the second allele-specific primer is positioned at the single nucleotide polymorphism nucleotide position.

5. A method for determining which single nucleotide polymorphism (SNP) variant of an allele from a gene isolated from a heterozygous patient is on the same mRNA transcript as a disease-causing mutation at a remote region of the gene's mRNA comprising
   (a) providing a first allele-specific primer which recognizes a first variant of a first SNP in the mRNA transcript of said heterozygous patient,
   (b) providing a second allele-specific primer which recognizes a second variant of said first SNP in the mRNA transcript of said heterozygous patient,
   (c) conducting a first reverse transcription reaction from said gene's mRNA using the allele-specific primer of part (a) to obtain a first subpopulation of allele-specific cDNA product or conducting a second reverse transcription reaction from said gene's mRNA using the allele-specific primer of part (b) to obtain a second subpopulation of allele-specific cDNA product, wherein the first subpopulation and second subpopulation are allele-specific for said first variant and said second variant, respectively;
   (d) providing a set of PCR primers flanking said disease-causing mutation and capable of hybridizing to said first or second subpopulation of allele-specific cDNA product, and
   (e) amplifying said remote region of the allele-specific cDNA product using said set of PCR primers to obtain a PCR product, wherein the first allele-specific primer and the second allele-specific primer is shorter than 18 nucleotides, and further comprising at least
   (f) providing a third allele-specific primer which recognizes one variant of a second single nucleotide polymorphism (second SNP), wherein said second SNP is different from said first SNP,
   (g) providing a fourth allele-specific primer which recognizes another variant of said second SNP,
   (h) conducting a reverse transcription reaction from said gene's mRNA using either the third allele-specific primer of part (f) or the fourth allele-specific primer of part (g) thereby generating an allele-specific cDNA product; and
   (i) amplifying said remote region of the allele-specific cDNA product of part (h) using said set of PCR primers, wherein the third allele-specific primer and the fourth allele-specific primer are shorter than 18 nucleotides.

6. The method of claim 5, wherein the said disease is Huntington's disease, and both of said first SNP and said second SNP are selected from rs1936032, rs4690074, rs363125, and rs362331.

7. The method of claim 5, further comprising at least:
   (j) providing a fifth allele-specific primer which recognizes one variant of a third single nucleotide polymorphism (third SNP), wherein said third SNP is different from the single nucleotide polymorphism and the second SNP,
   (k) providing a sixth allele-specific primer which recognizes another variant of said third SNP,
   (l) conducting a reverse transcription reaction from said gene's mRNA using either the allele-specific primer of part (j) or the allele-specific primer of part (k) thereby generating an allele-specific cDNA product; and
   (m) amplifying said remote region of the allele-specific cDNA product of part (l) using said set of PCR primers, wherein the fifth allele-specific primer and the sixth allele-specific primer is shorter than 18 nucleotides.

8. The method of claim 7, wherein the said disease is Huntington's disease, and said SNP, said second SNP and said third SNP are selected from rs1936032, rs4690074, rs363125, and rs362331.

9. The method of claim 8, further comprising:
   (n) providing a seventh allele-specific primer which recognizes one variant of a fourth single nucleotide polymorphism (fourth SNP), wherein said fourth SNP is different from the single nucleotide polymorphism, the second SNP, and the third SNP,
   (o) providing an eighth allele-specific primer which recognizes another variant of said fourth SNP,
   (p) conducting a reverse transcription reaction from said gene's mRNA using either the allele-specific primer of part (n) or the allele-specific primer of part (o) thereby generating an allele-specific cDNA product; and
   (q) amplifying said remote region of the allele-specific cDNA product of part (p) using said set of PCR primers, wherein the seventh allele-specific primer and the eighth allele-specific primer is shorter than 18 nucleotides.

10. The method of claim 9, wherein the said disease is Huntington's disease, and said SNP, said second SNP, said third SNP and said fourth SNP are selected from rs1936032, rs4690074, rs363125, and rs362331.

11. The method of claim 5, wherein step (h) is carried out by conducting a third reverse transcription reaction from said gene's mRNA using the third allele-specific primer of part (f) to obtain a third subpopulation of allele-specific cDNA product or a fourth reverse transcription reaction from said gene's mRNA using the fourth allele-specific primer of part (g) to obtain a fourth subpopulation of allele-specific cDNA product.

12. The method of claim 5, wherein said remote region is in the 5' direction from the site of said first SNP in the gene's mRNA.

13. The method of claim 12, wherein said remote region is at least 6.5 kb or more from the site of said first SNP.

14. The method of claim 5, wherein the PCR product obtained from step (e) does not include the site of said first SNP.

15. The method of claim 5, wherein step (c) is carried out by conducting said first reverse transcription reaction and conducting said second reverse transcription reaction in separate tubes.

* * * * *